(12) United States Patent
Wightman

(10) Patent No.: US 10,723,731 B2
(45) Date of Patent: *Jul. 28, 2020

(54) HETEROBIFUNCTIONAL LINKERS WITH POLYETHYLENE GLYCOL SEGMENTS AND IMMUNE RESPONSE MODIFIER CONJUGATES MADE THEREFROM

(71) Applicant: 3M INNOVATIVE PROPERTIES COMPANY, St. Paul, MN (US)

(72) Inventor: Paul D. Wightman, Louisville, KY (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/905,367

(22) Filed: Feb. 26, 2018

(65) Prior Publication Data

US 2018/0186792 A1 Jul. 5, 2018

Related U.S. Application Data

(63) Continuation of application No. 15/331,933, filed on Oct. 24, 2016, now Pat. No. 9,902,724, which is a continuation of application No. 14/123,727, filed as application No. PCT/US2012/040473 on Jun. 1, 2012, now Pat. No. 9,475,804.

(60) Provisional application No. 61/493,143, filed on Jun. 3, 2011, provisional application No. 61/493,051, filed on Jun. 3, 2011.

(51) Int. Cl.
*C07D 471/04* (2006.01)
*A61K 47/60* (2017.01)
*C07D 207/46* (2006.01)

(52) U.S. Cl.
CPC .......... *C07D 471/04* (2013.01); *A61K 47/60* (2017.08); *C07D 207/46* (2013.01)

(58) Field of Classification Search
CPC ... A61K 47/605; C07D 207/46; C07D 471/04
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,206,370 A | 4/1993 | Schwartz |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,605,899 A | 2/1997 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,679,778 A | 10/1997 | Abrams |
| 5,693,811 A | 12/1997 | Lindstrom |
| 5,714,608 A | 2/1998 | Gerster |
| 5,741,908 A | 4/1998 | Gerster et al. |

(Continued)

FOREIGN PATENT DOCUMENTS

| | | |
|---|---|---|
| EP | 0 394 026 | 10/1990 |
| EP | 1 104 764 | 6/2001 |

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.
Brennan et al., "Automated Bioassay of Interferons in Micro-test Plates.", *Biotechniques*, June/July, 78, 1983.
Testerman et al., "Cytokine Induction by the Immunomodulators Imiquimod and S-27609.", *Journal of Leukocyte Biology*, vol. 58, pp. 365-372, Sep. 1995.
Bachman et al., "Synthesis of Substituted Quinolylamines. Derivatives of 4-Amino-7-Chloroquinoline.", *J. Org. Chem.* 15, pp. 1278-1284 (1950).
Jain et al., "Chemical and Pharmacological Investigations of Some ω-Substituted Alkylamino-3-aminopyridines.", *J. Med. Chem.*, 11, pp. 87-92 (1968).

(Continued)

*Primary Examiner* — James H Alstrum-Acevedo
*Assistant Examiner* — Kaipeen E Yang

(57) ABSTRACT

Conjugates of an immune response modifier, a linker, and an antigen are disclosed. The linker is represented by formula:

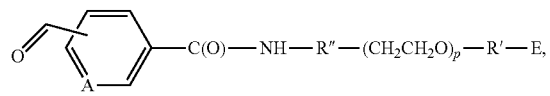

wherein A is CH or N, p is in a range from 1 to 50, R" is a bond or -alkylene-O—, R' is alkylene that is optionally interrupted or terminated with one or more amide or ether groups, and E is an amine- or thiol-reactive group. Pharmaceutical compositions containing the compound or the conjugate, methods of making a conjugate, and methods of use of the compounds or conjugates as immunomodulators for inducing cytokine biosynthesis in an animal and for vaccinating an animal are also disclosed. An antigen modified by the linker is also disclosed.

18 Claims, No Drawings

(56) References Cited

U.S. PATENT DOCUMENTS

| | | |
|---|---|---|
| 5,756,747 A | 5/1998 | Gerster et al. |
| 5,886,006 A | 3/1999 | Nikolaides et al. |
| 5,939,090 A | 8/1999 | Beaurline et al. |
| 6,028,076 A | 2/2000 | Hirota |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,113,918 A | 9/2000 | Johnson |
| 6,194,388 B1 | 2/2001 | Krieg |
| 6,194,425 B1 | 2/2001 | Gerster et al. |
| 6,200,592 B1 | 3/2001 | Tomai et al. |
| 6,207,646 B1 | 3/2001 | Krieg |
| 6,239,116 B1 | 5/2001 | Krieg |
| 6,245,776 B1 | 6/2001 | Skwierczynski et al. |
| 6,303,347 B1 | 10/2001 | Johnson |
| 6,329,381 B1 | 12/2001 | Kurimoto |
| 6,331,539 B1 | 12/2001 | Crooks et al. |
| 6,339,068 B1 | 1/2002 | Krieg |
| 6,365,166 B2 | 4/2002 | Beaurline et al. |
| 6,376,501 B1 | 4/2002 | Isobe |
| 6,376,669 B1 | 4/2002 | Rice et al. |
| 6,387,938 B1 | 5/2002 | Mizuguchi |
| 6,406,705 B1 | 6/2002 | Davis |
| 6,426,334 B1 | 7/2002 | Agrawal |
| 6,440,992 B1 | 8/2002 | Gerster et al. |
| 6,451,810 B1 | 9/2002 | Coleman et al. |
| 6,476,000 B1 | 11/2002 | Agrawal |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,028 B1 | 2/2003 | Johnson |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,784,188 B2 | 8/2004 | Crooks et al. |
| 6,797,718 B2 | 9/2004 | Dellaria et al. |
| 6,800,624 B2 | 10/2004 | Crooks et al. |
| 6,800,728 B2 | 10/2004 | Schwartz |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,462,689 B2 | 12/2008 | Schwartz |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,906,506 B2 | 3/2011 | Griesgraber et al. |
| 7,915,281 B2 | 3/2011 | Moser et al. |
| 7,923,560 B2 | 4/2011 | Wightman |
| 7,939,526 B2 | 5/2011 | Radmer et al. |
| 7,943,609 B2 | 5/2011 | Griesgraber et al. |

(56) References Cited

U.S. PATENT DOCUMENTS

| | | |
|---|---|---|
| 7,943,610 B2 | 5/2011 | Hays et al. |
| 7,943,636 B2 | 5/2011 | Hays et al. |
| 7,968,562 B2 | 6/2011 | Skwierczynski et al. |
| 7,968,563 B2 | 6/2011 | Kshirsager et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 8,034,938 B2 | 10/2011 | Griesgraber et al. |
| 8,138,173 B2 | 3/2012 | Merrill et al. |
| 8,143,270 B2 | 3/2012 | Kshirsager et al. |
| 8,158,794 B2 | 4/2012 | Kshirsager et al. |
| 8,178,677 B2 | 5/2012 | Kshirsager et al. |
| 8,263,594 B2 | 9/2012 | Lindstrom et al. |
| 8,343,993 B2 | 1/2013 | Kshirsager et al. |
| 8,658,666 B2 | 2/2014 | Rice et al. |
| 8,673,932 B2 | 3/2014 | Kshirsager et al. |
| 8,691,837 B2 | 4/2014 | Krepski et al. |
| 8,697,873 B2 | 4/2014 | Krepski et al. |
| 8,735,421 B2 | 5/2014 | Bonk et al. |
| 8,802,853 B2 | 8/2014 | Bonk et al. |
| 8,846,710 B2 | 9/2014 | Kshirsager et al. |
| 8,871,782 B2 | 10/2014 | Lindstrom et al. |
| 9,107,958 B2 | 8/2015 | Wightman |
| 9,475,804 B2 | 10/2016 | Wightman |
| 9,585,968 B2 | 3/2017 | Wightman |
| 9,801,947 B2 | 10/2017 | Miller |
| 9,902,724 B2 | 2/2018 | Wightman |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2003/0199461 A1 | 10/2003 | Averett |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0136065 A1 | 6/2005 | Valiante |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0175630 A1 | 8/2005 | Raz et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0078121 A1 | 4/2007 | Flynn et al. |
| 2007/0099901 A1 | 5/2007 | Krepski et al. |
| 2007/0123559 A1 | 5/2007 | Statham et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023722 A1 | 1/2009 | Coleman et al. |
| 2009/0030031 A1 | 1/2009 | Kshirsagar et al. |
| 2009/0035323 A1 | 2/2009 | Stoermer et al. |
| 2009/0075980 A1 | 3/2009 | Hays et al. |
| 2009/0105295 A1 | 4/2009 | Kshirsagar et al. |
| 2009/0124652 A1 | 5/2009 | Ach et al. |
| 2009/0163532 A1 | 6/2009 | Perman et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |
| 2017/0173164 A1 | 6/2017 | Wightman |

FOREIGN PATENT DOCUMENTS

| | | |
|---|---|---|
| JP | 9-176116 | 7/1997 |
| JP | 9-208584 | 8/1997 |
| JP | 11-080156 | 3/1999 |
| JP | 11-222432 | 8/1999 |
| JP | 2000-247884 | 9/2000 |
| JP | 2008-37799 | 2/2008 |
| WO | WO 2000-75304 | 12/2000 |
| WO | WO 2002-08905 | 1/2002 |
| WO | WO 2002-24225 | 3/2002 |
| WO | WO 2002-36592 | 5/2002 |
| WO | WO 2003-011223 | 2/2003 |
| WO | WO 2004-024889 | 3/2004 |
| WO | WO 2005-003064 | 1/2005 |
| WO | WO 2006-028451 | 3/2006 |
| WO | WO 2006-063072 | 6/2006 |
| WO | WO 2006-121528 | 11/2006 |
| WO | WO 2007-030775 | 3/2007 |
| WO | WO 2007-097934 | 8/2007 |
| WO | WO 2008-115319 | 9/2008 |

OTHER PUBLICATIONS

Baranov et al., "Pyrazoles, Imidazoles, and Other 5-Membered Rings.", *Chem. Abs.* 85, 94362, (1976).

Berényi et al., "Ring Transformation of Condensed Dihydro-as-triazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

(56) References Cited

OTHER PUBLICATIONS

Gundlach, "Synthesis and Evaluation of an Anti-MLCI × Anti-CD90 Bispecific Antibody for Targeting and Retaining Bone-Marrow-Derived Multipotent Stromal Cells in Infarcted Myocardium", Bioconjugate Chemistry, Jul. 2011, vol. 22, pp. 1706-1714.

Heil, "Species-Specific Recognition of Single-Stranded RNA via Toll-like Receptor 7 and 8", Science, Mar. 2004, vol. 303, No. 5663, pp. 1526-1529.

International Search Report for PCT International Application No. PCT/US2012/040473, dated Aug. 20, 2012, 4 pages.

Iyer, "Aromatic Aldehyde and Hydrazine Activated Peptide Coated Quantum Dots for Easy Bioconjugation and Live Cell Imaging", Bioconjugate Chemistry, May 2011, vol. 22, pp. 1006-1011.

Lagisetty, "Synthesis of radiolabeled cytarabine conjugates", Biorganic and Medicinal Chemistry Letters, Aug. 2009, vol. 19, No. 16, pp. 4764-4767.

Park, "Sodium Dithionite Reduction of Nitroarenes Using Viologen as an Electron Phase-Transfer Catalyst" Tetrahedron Letters, 1993, vol. 34, No. 46, pp. 7445-7446.

Pegurier, "Pyrazolone methylamino piperidine derivatives as novel CCR3 antagonists", Bioorganic and Medicinal Chemistry Letters, 2007, vol. 17, No. 15, pp. 4228-4231.

Phillips, "Single-Step Conjugation of Bioactive Peptides to Proteins via a Self-Contained Succinimidyl Bis-Arylhydrazone", Bioconjugate Chemistry, Oct. 2009, vol. 20(10) pp. 1950-1957.

Riener, "Heterobifunctional crosslinkers for tethering single ligand molecules to scanning probes", Analytica. Chimica Acta, 2003, vol. 497, No. 1-2, pp. 101-114.

Surrey, "The Synthesis of Some 3-Nitro- and 3-Amino-4-dialkylaminoalkylaminoquinoline Derivatives". Journal of the American Chemical Society, Jun. 1951, vol. 73, No. 6, pp. 2413-2416.

Supplemental European Search Report from Application No. EP12792340.7, dated Sep. 10, 2014, 3 pages.

Gerster et al. "Synthesis and Structure" J. Med Chem. 2005, 48, 3481-3491.

Wildling, "Linking of Sensor Molecules with Amino Groups to Amino-Functionalized AFM Tips", Bioconjugate Chemistry, Jul. 2011, vol. 22, pp. 1239-1248.

HETEROBIFUNCTIONAL LINKERS WITH POLYETHYLENE GLYCOL SEGMENTS AND IMMUNE RESPONSE MODIFIER CONJUGATES MADE THEREFROM

CROSS REFERENCE TO RELATED APPLICATIONS

This application is a continuation of U.S. application Ser. No. 15/331,933, filed Oct. 24, 2016, now U.S. Pat. No. 9,902,724, which is a continuation of U.S. application Ser. No. 14/123,727, filed Apr. 23, 2014, now U.S. Pat. No. 9,475,804, which is a national stage filing under 35 U.S.C. 371 of PCT/US2012/040473, filed Jun. 1, 2012, which claims priority to U.S. Provisional Application Nos.61/493,143 and 61/493,051, both filed Jun. 3, 2011, the disclosures of which are incorporated by reference in their entirety herein.

BACKGROUND

There has been an effort in recent years, with significant success, to discover new drug compounds that act by stimulating certain key aspects of the immune system, as well as by suppressing certain other aspects (see, e.g., U.S. Pat. No. 6,039,969 (Tomai et al.) and U.S. Pat. No. 6,200,592 (Tomai et al.). These compounds, referred to herein as immune response modifiers (IRMs), appear to act through basic immune system mechanisms known as Toll-like receptors (TLRs) to induce selected cytokine biosynthesis, induction of co-stimulatory molecules, and increased antigen-presenting capacity.

Many IRMs may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), $T_H2$-mediated diseases (e.g., asthma, allergic rhinitis, atopic dermatitis), and auto-immune diseases.

Many known IRMs are imidazoquinoline amine derivatives (see, e.g., U.S. Pat. No. 4,689,338 (Gerster)), but other compound classes are known as well (see, e.g., U.S. Pat. No. 5,446,153 (Lindstrom et al.); U.S. Pat. No. 6,194,425 (Gerster et al.); and U.S. Pat. No. 6,110,929 (Gerster et al.); and International Publication Number WO2005/079195 (Hays et al.)) while more are still being discovered.

Certain IRMs may also be useful, for example, as vaccine adjuvants. In some cases, an IRM compound may be administered in a conjugated composition in which the IRM compound is covalently attached to an antigenic moiety (see, e.g., U.S. Pat. No. 7,427,629 (Kedl et al.) and U. S. Pat. Appl. Pub. No. 2009/0035323 (Stoermer et al.)).

In view of the great therapeutic potential for IRMs in the treatment of a wide variety of diseases and conditions, and despite the important work that has already been done, there is still a need for expanded uses, compositions, and delivery options for IRM compounds.

SUMMARY

The present invention provides new conjugates that include an immune response modifier (IRM) portion. The new conjugates may be useful, for example, for generating an antigen-specific immune response. In one aspect, the present invention provides a conjugate comprising a reaction product of a hydrazine- or hydrazide-substituted immune response modifier; a linker represented by formula:

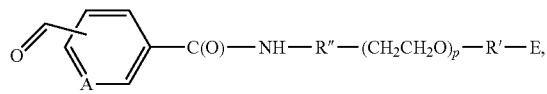

wherein A, p, R', R", and E are as defined below; and an antigen.

In another aspect, the present invention provides a conjugate comprising an immune response modifier; a linker represented by formula:

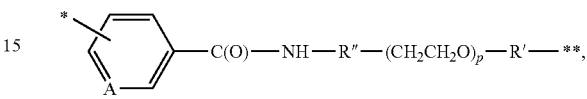

wherein A, p, R', and R" are as defined below; and an antigen; wherein the immune response modifier is covalently attached to the linker at * through a hydrazone functional group, and wherein the antigen is covalently attached to the linker at ** through an amide, disulfide, urea, thiourea, carbamate, or a carbon-sulfur or carbon-nitrogen bond alpha to an amide or sulfone or directly attached to a succinimide ring.

In another aspect, the present disclosure provides a method of making a conjugate, the method comprising combining an antigen with a linker to provide a modified antigen, wherein the linker is represented by formula:

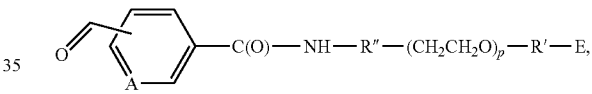

wherein A, p, R', R", and E are as defined below; and combining the modified antigen with a hydrazine- or hydrazide-substituted immune response modifier to provide the conjugate.

The conjugates of the present invention can induce cytokine biosynthesis (e.g., induce the synthesis of at least one cytokine) and otherwise modulate the immune response when administered to animals The ability to induce cytokine biosynthesis in animals makes the conjugates useful for treating a variety of conditions such as viral diseases and tumors that are responsive to such changes in the immune response. Accordingly, the present invention provides a method of inducing cytokine biosynthesis in an animal by administering to the animal an effective amount of a conjugate disclosed herein.

Co-delivering a vaccine adjuvant (e.g., an IRM compound such as a compound of Formula I or II described below) and an antigen to an immune cell can increase the immune response to the antigen and improve antigen-specific immunological memory. Optimal delivery may occur, for example, when the adjuvant and the antigen are processed within an antigen presenting cell at the same time, for example, when they are covalently attached as in the conjugates of the present invention. Accordingly, the present invention further provides a method of vaccinating an animal comprising administering to the animal a conjugate disclosed herein.

The invention further provides pharmaceutical compositions comprising a pharmaceutically acceptable carrier and an effective amount of a conjugate disclosed herein.

Advantageously, conjugates according to the present invention can be prepared under conditions that do not denature the antigens (e.g., which may be proteins). For example, the conjugates can be prepared at physiological pH. Furthermore, the covalent bonds formed to make the conjugates do not require irradiation. The linker used to make the conjugates is advantageous, for example, for promoting solubility and stability of the antigen (e.g., which in some embodiments is a protein). Accordingly, in certain embodiments, the present invention further provides a compound represented by formula:

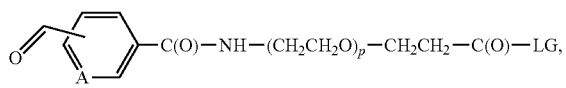

wherein A, p, and LG are as defined below; and a modified antigen having at least one segment represented by formula:

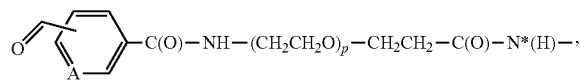

wherein A and p are as defined below, and the nitrogen atom indicated by N* is covalently bonded to the antigen.

Also advantageously, in many embodiments, including embodiments wherein the hydrazine- or hydrazide-substituted immune response modifier comprises an aromatic ring to which the hydrazine or hydrazide group is bonded, the formation of the conjugate can be easily monitored using UV spectroscopy due to the characteristic absorption of the hydrazone bond that is formed.

The terms "comprises" and variations thereof do not have a limiting meaning where these terms appear in the description and claims.

As used herein, "a", "an", "the", "at least one", and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

"Antigen" refers to any substance that may be bound by an antibody in a manner that is immunospecific to some degree for a humoral immune response. "Antigen" as used herein also refers to any substance that may be bound by an antigen-presenting cell for a cell-mediated immune response. An antigen described herein may elicit antigenic activity including, for example, any one or more of the following: generation of antibodies specific to the antigen by B cells, immune cell maturation, cytokine production by immune cells, and generation of antigen-presenting cells that present the antigen. Antigens useful for practicing the present disclosure include those that have very weak activity and/or no therapeutic benefit in the absence of an adjuvant (e.g., such as an IRM compound).

A "conjugate" as used herein is a compound containing two components (e.g., an IRM compound and an antigen) covalently linked together.

"Induce" and variations thereof refer to any measurable increase in cellular activity. For example, induction of an immune response may include, for example, an increase in the production of a cytokine, activation, proliferation, or maturation of a population of immune cells, and/or other indicator of increased immune function.

The term "protein" includes proteins and glycoproteins. For proteinaceous antigens, modifications can be made to a particular antigen without rendering the modified antigen unsuitable for use as an antigen. For example, one or more potions of the amino acid sequence of a proteinaceous antigen may be deleted or substituted or additional amino acids may be added, and the proteinaceous antigen can still retain antigenic activity.

The term "hydrazine" refers to a functional group of the formula —NHNH$_2$.

The term "hydrazide" refers to a functional group of the formula —C(O)NHNH$_2$.

The term "hydrazone" refers to a functional group of the formula —NHN=C(R)— or —C(O)NHN=C(R)—, wherein R is hydrogen or alkyl, for example.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION

In one embodiment, the present invention provides a conjugate comprising a reaction product of:
a hydrazine- or hydrazide-substituted immune response modifier;
a linker represented by formula:

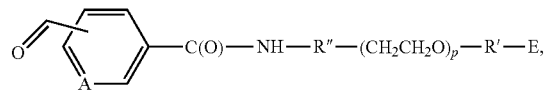

wherein A is CH or N, p is in a range from 1 to 50, R" is a bond or -alkylene-O—, R' is alkylene that is optionally interrupted or terminated with one or more amide or ether groups, and E is an amine- or thiol-reactive group; and
an antigen.

In one embodiment, the present invention provides a conjugate comprising:
an immune response modifier;
a linker represented by formula:

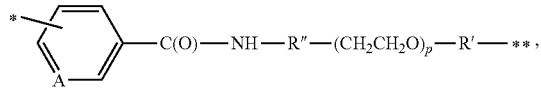

wherein A is CH or N, p is in a range from 1 to 50, R" is a bond or -alkylene-O—, and R' is alkylene that is optionally interrupted or terminated with one or more amide or ether groups; and
an antigen; wherein the immune response modifier is covalently attached to the linker at * through a hydrazone functional group, and wherein the antigen is covalently attached to the linker at **.

The present invention further provides a method of making a conjugate, the method comprising:

combining an antigen with a linker to provide a modified antigen, wherein the linker is represented by formula:

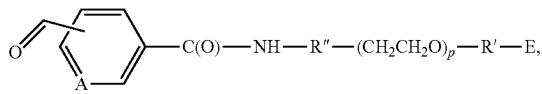

wherein A is CH or N, p is in a range from 1 to 50, R" is a bond or -alkylene-O—, R' is alkylene that is optionally interrupted or terminated with one or more amide or ether groups, and E is an amine- or thiol-reactive group; and combining the modified antigen with a hydrazine- or hydrazide-substituted immune response modifier to provide the conjugate.

For any of the conjugates presented herein, each one of the following variables (e.g., A, p R', E, $R_2$, $R_3$, X, Y, n, and so on) in any of its embodiments can be combined with any one or more of the other variables in any of their embodiments and associated with any one of the formulas or IRM compounds described herein, as would be understood by one of skill in the art. Each of the resulting combinations of variables is an embodiment of the present invention.

In some embodiments, A is CH or N. In some embodiments, A is CH.

In some embodiments, including any of the above embodiments of conjugates where A is defined, p is in a range from 1 to 50. In some embodiments, p is in a range from 2 to 50. In some embodiments, p is in a range from 1 to 40. In some embodiments, p is in a range from 2 to 40. In some embodiments, p is in a range from 1 to 30. In some embodiments, p is in a range from 2 to 30. In some embodiments, p is in a range from 2 to 24. In some embodiments, p is in a range from 2 to 16. In some embodiments, p is in a range from 2 to 12. In some embodiments, p is in a range from 4 to 24. In some embodiments, p is in a range from 4 to 16. In some embodiments, p is in a range from 4 to 12.

In some embodiments, including any of the above embodiments of conjugates where A or p is defined, R' alkylene that is optionally interrupted or terminated with one or more amide or ether groups. In some of these embodiments, R' is ethylene. In some of these embodiments, R' is propylene. In some embodiments, R' is alkylene that is interrupted by one or two amide groups.

In some embodiments, including any of the above embodiments of conjugates where A, p, or R' is defined, R" is a bond or -alkylene-O—. In some embodiments, R" is a bond. In these embodiments, it will be understood that R" would be absent from the structural formula of the linker. In some embodiments, R" is -propylene-O—.

In some embodiments, including any of the above embodiments of conjugates where A, p, R', or R" is defined, E is an amine- or thiol-reactive group. Suitable amine- or thiol-reactive groups include maleimide, vinylsulfone, acrylamide, pyridyldisulfide, methyl sulfonyl disulfide, N-hydroxysuccinimide ester, sulfo-N-hydroxysuccinimide ester or a salt thereof, 4-nitrophenyl ester, acid chloride, acid bromide, acid anhydride, pentafluorophenyl ester, tetrafluorophenyl ester, N-hydroxybenzotriazole ester, iodoacetyl, bromoacetyl, chloroacetyl, succinimidyl carbonate, chloroformate, —OC(O)—O—CH(Cl)CCl$_3$, —OC(O)—O-(4-nitrophenyl), isocyanate, and thioisocyanate groups.

In some embodiments, including any of the above embodiments of conjugates where A, p, R', or R" is defined, E is an ester selected from the group consisting of N-hydroxysuccinimide ester, sulfo-N-hydroxysuccinimide ester or a salt thereof, 4-nitrophenyl ester, pentafluorophenyl ester, tetrafluorophenyl ester, and N-hydroxybenzotriazole ester. That is, E is N-succinimidyloxycarbonyl, p-nitrophenoxycarbonyl, pentafluorophenoxycarbonyl, tetrafluorophenoxycarbonyl, N-benzotriazolyloxycarbonyl, or sulfo-N-succinimidyloxycarbonyl or a sodium salt thereof.

As defined above, "antigen" refers to any substance that may be bound in a manner that is immunospecific to some degree and may elicit a humoral immune response, a cell-mediated response, or both. Exemplary antigens include peptide, polypeptide, protein, glycoprotein, lipid, glycolipid, polysaccharide, carbohydrate, polynucleotide, prions, oligonucleotide (e.g., CpG), DNA, virus, bacteria, fungus, parasite, toxin, or toxoid).

In some embodiments, including any of the above embodiments of conjugates where A, p, R', R", or E is defined, the antigen is a protein.

In some embodiments, including any of the above embodiments of conjugates where A, p, R', R", or E is defined, the antigen is a lipid.

In some embodiments, including any of the above embodiments of conjugates where A, p, R', R", or E is defined, the antigen is a vaccine.

In some embodiments, including any of the above embodiments of conjugates where A, p, R', R", or the antigen is defined, the antigen is covalently attached to the linker at  through an amide, disulfide, urea, thiourea, carbamate, or a carbon-sulfur or carbon-nitrogen bond alpha to an amide or sulfone or directly attached to a succinimide ring. In some embodiments, the antigen is covalently attached to the linker at  through an amide or a carbon-sulfur or carbon-nitrogen bond alpha to an amide or sulfone or directly attached to a succinimide ring. In some embodiments, the antigen is covalently attached to the linker at ** through an amide functional group.

In some embodiments, the linker is a compound represented by formula:

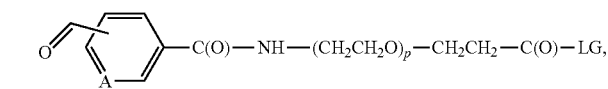

wherein A is CH or N, p is in a range from 1 to 50, and LG is a group that can be displaced by an amine When this linker is used to modify an antigen, a modified antigen having at least one segment represented by formula may be provided:

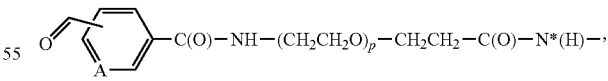

wherein A is CH or N, p is in a range from 1 to 50, and the nitrogen atom indicated by N* is covalently bonded to the antigen.

In some embodiments of the linker or modified antigen, A is CH or N. In some embodiments, A is CH.

In some embodiments, including any of the above embodiments of the linker or modified antigen where A is defined, p is in a range from 1 to 50. In some embodiments, p is in a range from 2 to 50. In some embodiments, p is in a range from 1 to 40. In some embodiments, p is in a range from 2 to 40. In some embodiments, p is in a range from 1 to 30. In some embodiments, p is in a range from 2 to 30. In some embodiments, p is in a range from 2 to 24. In some embodiments, p is in a range from 2 to 16. In some embodiments, p is in a range from 2 to 12. In some embodiments, p is in a range from 4 to 24. In some embodiments, p is in a range from 4 to 16. In some embodiments, p is in a range from 4 to 12.

In some embodiments, including any of the above embodiments of the linker where A or p is defined, LG is a group that can be displaced by an amine. In some embodiments, LG is selected from the group consisting of N-succinimidyloxy, p-nitrophenoxy, pentafluorophenoxy, tetrafluorophenoxy, N-benzotriazolyloxy, and sulfo-N-succinimidyloxy or a sodium salt thereof. In some embodiments, LG is —Cl, —Br, or —I.

In the modified antigen, the antigen may be any of those described above. In some embodiments, including any of the above embodiments of modified antigens where A or p is defined, the antigen is a protein.

In some embodiments, including any of the above embodiments of conjugates where A or p is defined, the antigen is a lipid.

In some embodiments, including any of the above embodiments of conjugates where A or p is defined, the antigen is a vaccine.

Any suitable IRM compound may be useful for providing the conjugates of the present invention.

Suitable IRM compounds include small organic molecules, i.e., molecules having a molecular weight of less than about 1000 Daltons, although in some embodiments a suitable IRM compound may have a molecular weight of less than about 700 Daltons. In some embodiments, a suitable IRM compound may have a molecular weight from about 500 Daltons to about 700 Daltons, while in other embodiments, a suitable IRM compound may have a molecular weight from about 250 to about 500 Daltons.

Suitable IRMs include compounds disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; and 6,818,650; U.S. Patent Publication Nos. 2004/0091491; 2004/0147543; 2004/0176367; and 2006/0100229; and International Publication Nos. WO2005/18551, WO2005/18556, WO2005/20999, WO2005/032484, WO2005/048933, WO2005/048945, WO2005/051317, WO2005/051324, WO2005/066169, WO2005/066170, WO2005/066172, WO2005/076783, WO2005/079195, WO2005/094531, WO2005/123079, WO2005/123080, WO2006/009826, WO2006/009832, WO2006/026760, WO2006/028545, WO2006/028962, WO2006/029115, WO2006/038923, WO2006/065280, WO2006/074003, WO2006/083440, WO2006/086449, WO2006/086633, WO2006/086634, WO2006/091394, WO2006/091567, WO2006/091568, WO2006/091647, WO2006/093514, WO2006/098852, WO2006/107771, WO2006/107851, and WO2006/107853.

Additional examples of suitable small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U. S. Pat. Nos. 6,376,501; 6,028,076 and 6,329,381; and in WO2002/08905), certain 3-β-D-ribofuranosylthiazolo[4,5-d]pyrimidine derivatives (such as those described in U.S. Publication No. 2003/0199461), and certain small molecule immuno-potentiator compounds such as those described, for example, in US2005/0136065.

Other suitable IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO2000/75304. Still other IRM nucleotide sequences include guanosine- and uridine-rich single-stranded RNA (ssRNA) such as those described, for example, in Heil et al., *Science*, vol. 303, pp. 1526-1529, Mar. 5, 2004.

Other suitable IRMs include biological molecules such as aminoalkyl glucosaminide phosphates (AGPs) and are described, for example, in U.S. Pat. Nos. 6,113,918; 6,303,347; 6,525,028; and 6,649,172.

In some embodiments of the present invention, a suitable IRM compound may be an agonist of at least one TLR such as TLR7 or TLR8. In some embodiments, the IRM may also be an agonist of TLR 9.

In some embodiments of the present invention, a suitable IRM compound may include a 2-aminopyridine ring fused to a five membered nitrogen-containing heterocyclic ring, or a 4-aminopyrimidine fused to a five membered nitrogen-containing heterocyclic ring.

Suitable IRM compounds include compounds containing a 2-aminopyridine ring fused to a five membered nitrogen-containing heterocyclic ring. Such compounds include imidazoquinoline amines, for example, substituted imidazoquinoline amines such as amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines such as amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines such as amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

In some embodiments, the IRM compound is an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, a pyrazolopyridine amine, a pyrazoloquinoline amine, a tetrahydropyrazoloquinoline amine, a pyrazolonaphthyridine amine, or a tetrahydropyrazolonaphthyridine amine.

In some embodiments, the IRM compound is a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, a pyrazolopyridine amine, a pyrazoloquinoline amine, a tetrahydropyrazoloquinoline amine, a pyrazolonaphthyridine amine, or a tetrahydropyrazolonaphthyridine amine.

In some embodiments, the IRM compound is an imidazoquinoline amine, imidazonaphthyridine amine, pyrazoloquinoline amine, pyrazolonaphthyridine amine, or a thiazoloquinoline amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amine, a hydroxylamine substituted imidazoquinoline amine, an oxime substituted imidazoquinoline amine, a 6-, 7-, 8-, or 9-aryl, heteroaryl, aryloxy or arylalkyleneoxy substituted imidazoquinoline amine, or an imidazoquinoline diamine In some embodiments, substituted imidazoquinoline amines exclude 1-(2-methylpropyl)-1H-imidazo[4,5-c]quinolin-4-amine and 4-amino-α, α-dimethyl-2-ethoxymethyl-1H-imidazo[4,5-c]quinolin-1-ethanol.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

IRM compounds, including any of the specific IRM compounds described above, include a hydrazine or hydrazide substituent. The hydrazine or hydrazide substituent may be attached to the IRM compound (e.g., in some embodiments, an imidazoquinoline amine, imidazonaphthyridine amine, imidazopyridine amine, pyrazoloquinoline amine, pyrazolonaphthyridine amine, or pyrazolopyridine amine) at the 1-position. In some of these embodiments, the IRM is of the formula I or II:

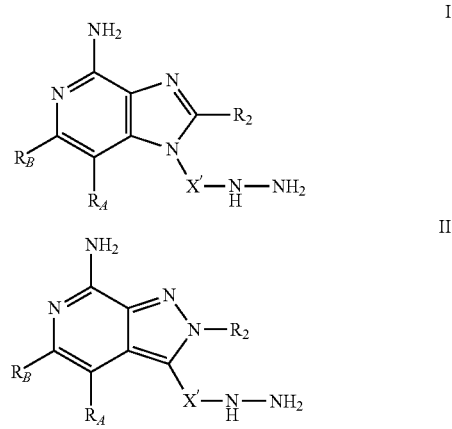

wherein
$R_A$ and $R_B$ are each independently selected from the group consisting of:
hydrogen,
halogen,
alkyl,
alkenyl,
alkoxy,
alkylthio, and
—$N(R_9)_2$;
or when taken together, $R_A$ and $R_B$ form a fused heteroaryl ring containing one heteroatom selected from the group consisting of N and S or a fused aryl ring wherein the aryl or heteroaryl ring is unsubstituted or substituted by one or more R groups, or substituted by one $R_3$ group, or substituted by one $R_3$ group and one R group;
or when taken together, $R_A$ and $R_B$ form a fused 5 to 7 membered saturated ring, optionally containing one heteroatom selected from the group consisting of N and S, and unsubstituted or substituted by one or more R groups;
R is selected from the group consisting of:
halogen,
hydroxy,
alkyl,
alkenyl,
haloalkyl,
alkoxy,
alkylthio, and
—$N(R_9)_2$;
$R_2$ is selected from the group consisting of:
amino,
—$R_4$,
—X—$R_4$,
—X—Y—$R_4$, and
—X—$R_5$;

$R_3$ is selected from the group consisting of:
- —Z—$R_4$,
- —Z—X—$R_4$,
- —Z—X—Y—$R_4$,
- —Z—X—Y—X—Y—$R_4$, and
- —Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene, interrupted by one or more —O— groups, or terminated by —O— or —N(H)—;

Y is selected from the group consisting of:
- —O—,
- —S(O)$_{0-2}$—,
- —S(O)$_2$—N($R_8$)—,
- —C($R_6$)—,
- —C($R_6$)—O—,
- —O—C($R_6$)—,
- —O—C(O)—O—,
- —N($R_8$)-Q-,
- —C($R_6$)—N($R_8$)—,
- —O—C($R_6$)—N($R_8$)—,
- —C($R_6$)—N(O$R_9$)—,
- —O—N($R_8$)-Q-,
- —O—N=C($R_4$)—,
- —C(=N—O—$R_8$)—,
- —CH(—N(—O—$R_8$)-Q-$R_4$)—,

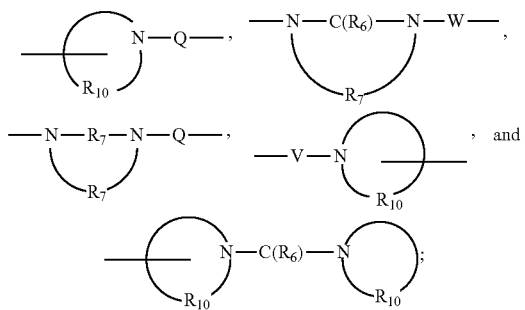

X' is selected from the group consisting of —X—, —X—C(O)—, —X—Y—X—, and —X—Y—X—C(O)—;

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

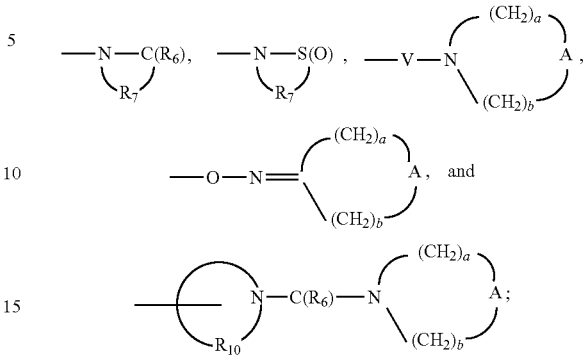

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N($R_4$)—;
A' is selected from the group consisting of —O—, —S(O)$_{0-2}$—, —N(-Q-$R_4$)—, and —CH$_2$—; Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$;
W is selected from the group consisting of a bond, —C(O)—, and —S(O)$_2$—; and
a and b are independently integers from 1 to 6 with the proviso that a+b is ≤7.

As used herein, the terms "alkyl", "alkenyl", "alkynyl", and the prefix "alk-" are inclusive of both straight chain and branched chain groups and of cyclic groups, e.g. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 7 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups include chloromethyl and trifluoromethyl.

An alkylene group with carbon atoms optionally "interrupted" by —O— refers to having carbon atoms on either side of the —O—. An example is —CH$_2$—CH$_2$—O—CH$_2$—CH$_2$—.

An alkylene group with carbon atoms optionally "terminated" by —O— refers to having the —O— on either end of the alkylene group or chain of carbon atoms. Examples include —O—CH$_2$—CH$_2$—CH2—CH$_2$— and —CH$_2$—CH$_2$—CH$_2$—CH$_2$—O—. In the compounds of Formulas I and II and conjugates of the present invention, when X' is alkylene terminated by —O—, the —O— may be connected to either the nitrogen of the imidazole ring or the Y group. In the compounds of Formulas I and II and conjugates of the present invention, when X' is alkylene terminated by —N(H)—, the —N(H)— is typically connected to the imidazole ring.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N(R$_8$)—C(O)—N(R$_8$)— each R$_8$ group is independently selected. In another example, when two R$_{10}$ groups are present each R$_{10}$ group is independently selected.

In some embodiments of Formulas I and II, when taken together, R$_A$ and R$_B$ form a fused aryl ring that is unsubstituted. In some of these embodiments, the fused aryl ring is a fused benzene ring.

In some embodiments of Formulas I and II, including embodiments where R$_A$ and R$_B$ are defined as above, R$_2$ is hydrogen, amino, alkyl, alkoxyalkylenyl, alkylaminoalkylenyl, or hydroxyalkylenyl.

In some embodiments of Formulas I and II, including embodiments where R$_A$ and R$_B$ are defined as above, R$_2$ is hydrogen, alkyl, alkoxyalkylenyl, or hydroxyalkylenyl.

In some embodiments of Formulas I and II, including embodiments where R$_A$ and R$_B$ are defined as above, R$_2$ is hydrogen, alkyl, or alkoxyalkylenyl.

In some embodiments of Formulas I and II, including embodiments where R$_A$ and R$_B$ and R$_2$ are defined as above, X' is —X$^1$—Y—X$^2$— or —X$^1$—Y—X$^2$—C(O)—, wherein X$^1$ is alkylene optionally interrupted by one or more —O— groups and optionally terminated by —O—; Y is —NH—C(O)—, and X$^2$ is alkylene, arylene, or heteroarylene.

In some embodiments of Formulas I and II, including embodiments where R$_A$ and R$_B$ and R$_2$ are defined as above, X' is —X$^1$—Y—X$^2$—, wherein X$^1$ is alkylene optionally interrupted by one or more —O— groups and optionally terminated by —O—; Y is —NH—C(O)—, and X$^2$ is phenylene or pyridylene.

In some embodiments, compounds of Formula I are described in co-pending U.S. patent application Ser. No. 61/493,051, filed Jun. 3, 2011, and incorporated herein by reference in its entirety.

In some embodiments, the compound of Formula I is N-(4-{[4-amino-2-butyl-1H-imidazo[4,5-c]quinolin-1-yl]oxy}butyl)-6-hydazinonicotinamide:

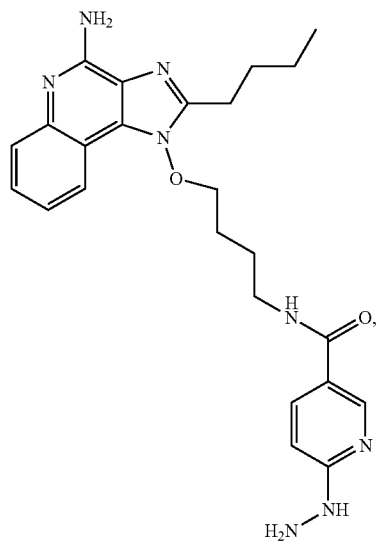 [SMILES: CCCCc1nc2c(N)nc3ccccc3c2n1OCCCCNC(=O)c1ccc(NN)nc1]

or a pharmaceutically acceptable salt thereof.

In some embodiments, the compound of Formula I is N-(4-{[4-amino-2-butyl-1H-imidazo[4,5-c]quinolin-1-yl]oxy}butyl)-6-(N'-isopropylidenehydrazino)nicotinamide:

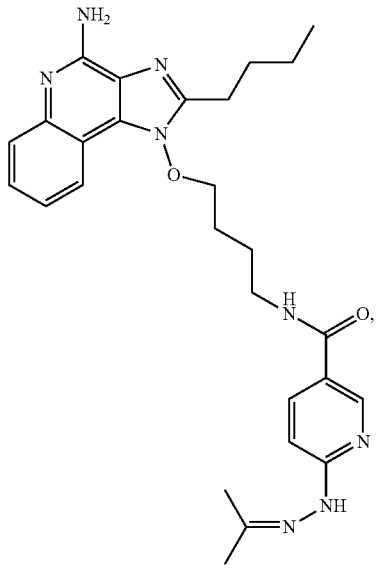 [SMILES: CCCCc1nc2c(N)nc3ccccc3c2n1OCCCCNC(=O)c1ccc(NN=C(C)C)nc1]

or a pharmaceutically acceptable salt thereof.

In some embodiments, the compound of Formula I is N-{2-[4-Amino-2-(ethoxymethyl)-1H-imidazo[4,5-c]quinolin-1-yl]-1,1-dimethylethyl}-4-hydrazino-4-oxobutanamide:

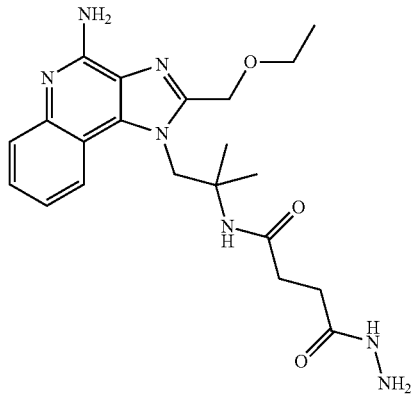 [SMILES: CCOCc1nc2c(N)nc3ccccc3c2n1CC(C)(C)NC(=O)CCC(=O)NN]

or a pharmaceutically acceptable salt thereof.

In some embodiments, the compound of Formula I is N-(4-{[4-amino-2-butyl-1H-imidazo[4,5-c]quinolin-1-yl]oxy}butyl)-4-(N'-isopropylidenehydrazino)benzamide:

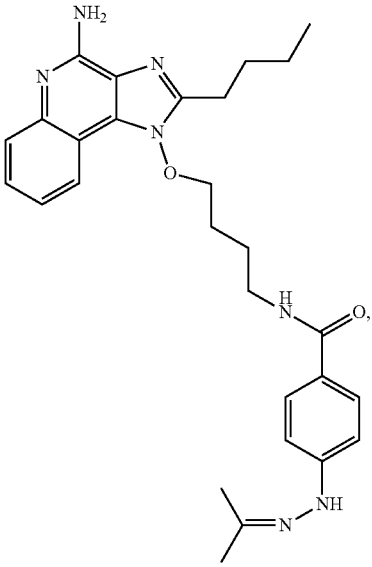 [SMILES: CCCCc1nc2c(N)nc3ccccc3c2n1OCCCCNC(=O)c1ccc(NN=C(C)C)cc1]

or a pharmaceutically acceptable salt thereof.

In some embodiments, the compound of Formula I is N-(4-{[4-amino-2-butyl-1H-imidazo[4,5-c]quinolin-1-yl]oxy}butyl)-4-hydazinobenzamide:

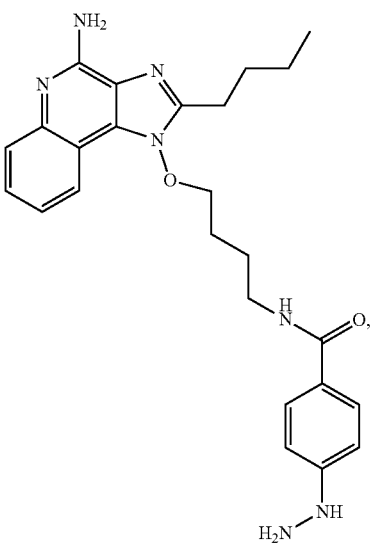 [SMILES: CCCCc1nc2c(N)nc3ccccc3c2n1OCCCCNC(=O)c1ccc(NN)cc1]

or a pharmaceutically acceptable salt thereof.

The hydrazine or hydrazide substituent may be attached to the IRM compound (e.g., in some embodiments, an imidazoquinoline amine, imidazonaphthyridine amine, pyrazoloquinoline amine, pyrazolonaphthyridine amine, or thiazoloquinoline amine) at the 7-position or 8-position. In some embodiments, the IRM is of the formula III, IV, or V:

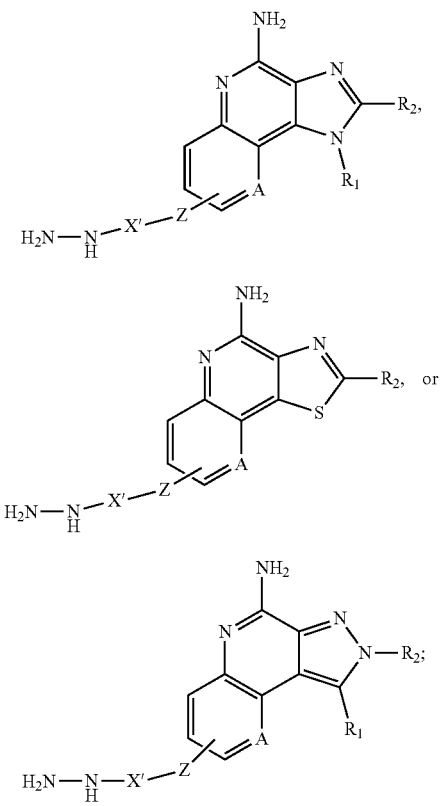

wherein $R_2$, X', and Z are as defined above, A is CH or N, and $R_1$ is selected from the group consisting of:
—N(H)—$R_4$,
—O—$R_4$,
—$R_4$,
—X—$R_4$,
—X—Y—$R_4$,
—N(H)—X—Y—$R_4$,
—X—Y—X—Y—$R_4$, and
—X—$R_5$;
wherein X, Y, $R_4$, and $R_5$ are as defined above.

In some embodiments of Formulas III, IV, and V, the —Z—X'—NHNH$_2$ group is bonded to the 7-position. In some embodiments of Formulas III, IV, and V, the —Z—X'—NHNH$_2$ group is bonded to the 8-position.

In some embodiments of Formulas III, IV, and V, including any of the above embodiments, A is CH. In other embodiments, A is N.

In some embodiments of Formulas III, IV, and V, including embodiments where A is defined as above, $R_2$ is hydrogen, amino, alkyl, alkoxyalkylenyl, alkylaminoalkylenyl, or hydroxyalkylenyl.

In some embodiments of Formulas III, IV, and V, including embodiments where A is defined as above, $R_2$ is hydrogen, alkyl, alkoxyalkylenyl, or hydroxyalkylenyl.

In some embodiments of Formulas III, IV, and V, including embodiments where A is defined as above, $R_2$ is hydrogen, alkyl, or alkoxyalkylenyl.

In some embodiments of Formulas III, IV, and V, including embodiments where A and $R_2$ are defined as above, Z is —O—. In some embodiments, Z is a bond.

In some embodiments of Formulas III, IV, and V, including embodiments where A, Z, and $R_2$ are defined as above, X' is —$X^1$—Y—$X^2$— or —$X^1$—Y—$X^2$—C(O)—, wherein $X^1$ is alkylene optionally interrupted by one or more —O— groups and optionally terminated by —O—; Y is —NH—C(O)—, and $X^2$ is alkylene, arylene, or heteroarylene.

In some embodiments of Formulas III, IV, and V, including embodiments where A, Z, and $R_2$ are defined as above, X' is —$X^1$—Y—$X^2$—, wherein $X^1$ is alkylene optionally interrupted by one or more —O— groups and optionally terminated by —O—; Y is —NH—C(O)—, and $X^2$ is phenylene or pyridylene.

In some embodiments of Formulas III, IV, and V, including embodiments where A, Z, X', and $R_2$ are defined as above, $R_1$ is selected from the group consisting of alkyl, arylalkylenyl, aryloxyalkylenyl, hydroxyalkyl, dihydroxyalkyl, alkylsulfonylalkylenyl, —X—Y—$R_4$, —X—$R_5$, and heterocyclylalkylenyl, wherein the heterocyclyl of the heterocyclylalkylenyl group is optionally substituted by one or more alkyl groups; wherein X is alkylene; Y is —N($R_8$)—C(O)—, —N($R_8$)—S(O)$_2$—, —N($R_8$)—C(O)—N($R_8$)—, or

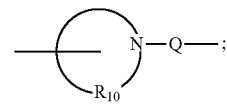

$R_4$ is alkyl, aryl, or heteroaryl; and $R_5$ is

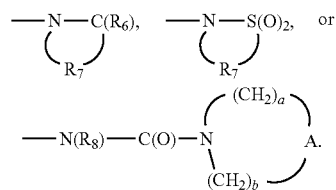

In some embodiments of Formulas III, IV, and V, including embodiments where A, Z, X', and $R_2$ are defined as above, $R_1$ is selected from the group consisting of 2-hydroxy-2-methylpropyl, 2-methylpropyl, propyl, ethyl, methyl, 2,3-dihydroxypropyl, 2-phenoxyethyl, 4-[(methylsulfonyl)amino]butyl, 2-methyl-2-[methylsulfonyl)amino]propyl, 2-(acetylamino)-2-methylpropyl, 2-{[(isopropylamino)carbonyl]amino}-2-methylpropyl, 4-{[(isopropylamino)carbonyl]amino)}butyl, 4-(1,1-dioxidoisothiazolidin-2-yl)butyl, tetrahydro-2H-pyran-4-ylmethyl, and (2,2-dimethyl-1,3-dioxolan-4-yl)methyl.

Preparation of the Conjugates

IRM compounds and linkers useful for practicing the present invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the IRM compounds and linkers useful for practicing the present invention as well as key intermediates. For more detailed description of the individual reaction steps, see the EXAMPLES section below. Those skilled in the art will appreciate that other synthetic routes may be used to synthesize the IRM compounds and linkers. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of IRM compounds and linkers useful for practicing the present invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate IRM compounds and linkers, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

In Reaction Scheme I, intermediate compounds useful for preparing hydrazine- or hydrazide-substituted immune response modifiers are described. In step (1) of Reaction Scheme I, the hydrazinobenzoic acid or hydrazinonicotinic acid compound of Formula VIII is reacted with acetone at ambient temperature to provide the hydrazone substituted compound of Formula IX. The starting hydrazine substituted compounds of Formula VIII are 4-hydrazinobenzoic acid (VIII where A=CH) and 6-hydrazinonicotinic acid (VIII where A=N). These compounds can be prepared using the reaction conditions described by Lagisetty, P.; Vilekar, P.; and Awasthi, V. *Biorganic and Medicinal Chemistry Letters*, 19, pp. 4764-4767 (2009) or Pegurier, C.; Collart, P.; Danhaive, P.; Defays, S.; Gillard, M.; Gilson, F.; Kogej, T.; Pasau, P.; Van Houtvin, N.; Van Thuyne, M.; Van Keulen, B. *Bioorganic and Medicinal Chemistry Letters*, 17, pp. 4228-4231 (2007); or reported in WO2006071940 (Flynn et al.).

In step (2) of Reaction Scheme I, the compound of Formula IX is reacted at ambient temperature with N-hydroxysuccinimide and a standard coupling reagent such as 1,3-dicyclohexylcarbodiimide (DCC) or 1-[3-(dimethylamino)propyl]-3-ethylcarbodiimide (EDC) in a suitable solvent such as dichloromethane or pyridine. The product of Formula X can be isolated using conventional means.

In step (3) of Reaction Scheme I, the hydrazinobenzoic acid or hydrazinonicotinic acid compound of Formula XI is reacted with acetone at ambient temperature to provide the hydrazone substituted compound of Formula XII. The starting hydrazine substituted compounds of Formula XI are 3-hydrazinobenzoic acid (XI where A=CH) and 5-hydrazinonicotinic acid (XI where A=N). These compounds can be prepared according to the procedures in the references provided to prepare the compounds of Formula VIII.

In step (4) of Reaction Scheme I, the compound of Formula XII is reacted at ambient temperature with N-hydroxysuccinimide using, for example, the conditions described above for step (2).

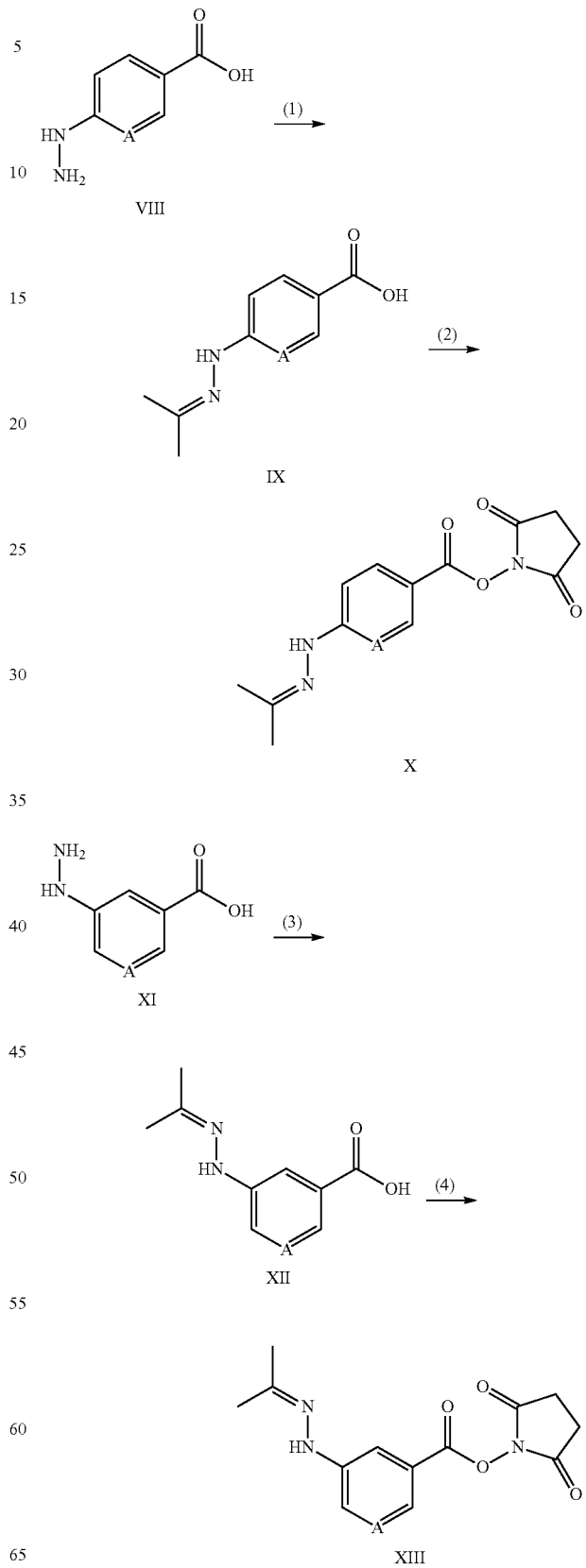

Reaction Scheme I

In some embodiments, IRM compounds useful for making conjugates of the present invention can be prepared according to Reaction Scheme II wherein $R_A$, $R_B$, and $R_2$ are as defined above, $X^1$ is alkylene optionally interrupted by one or more —O— groups and optionally terminated by —O—; and A is CH or N.

In step (1) of Reaction Scheme II, a compound of Formula XIV is reacted with a compound of Formula IX (from Reaction Scheme I where A=CH or N) to provide a compound of Formula XV. The reaction can be conducted at ambient temperature in a solvent such as dichloromethane, pyridine, or 1-butanol with a standard coupling reagent such as 1,3-dicyclohexylcarbodiimide (DCC) or 1-[3-(dimethylamino)propyl]3-ethylcarbodiimide (EDC). A compound of Formula XV can be isolated using conventional methods. As an alternative method for step (1) of Reaction Scheme II, a compound of Formula XIV is reacted with a compound of Formula X (from Reaction Scheme I where A=CH or N) to provide a compound of Formula XV. The compound of Formula XIV can be dissolved in a suitable alcoholic solvent such a 1-butanol and the compound of Formula X can be slowly added at ambient temperature.

Several compounds of Formula XIV are known and/or methods of their preparation have been described; see for example, U.S. Pat. No. 7,648,997 (Kshirsagar, et al.); U.S. Pat. No. 6,660,747 (Crooks, et al.); U.S. Pat. No. 6,069,149 (Nanba); U.S. Pat. No. 7,579,359 (Krepski et al.); U.S. Pat. No. 7,163,947 (Griesgraber et al.), and Int. Pat. App. Pub. No. WO 2006/029115 (Kshirsagar et al.).

In step (2) of Reaction Scheme II, the acetamine protecting group is removed under acidic conditions to provide the compound of Formula XVI, which is a subgenus of Formula I. The reaction can be conducted in hydrochloric acid at ambient or elevated temperature (e.g. 60° C.). A product of Formula XVI can be isolated, for example, as a hydrochloride salt by lyophilization.

In step (1a) of Reaction Scheme II, a compound of Formula XIV is reacted with a compound of either Formula XII or Formula XIII (from Reaction Scheme I where A=CH or N) according to the corresponding procedure described in step (1) to provide a compound of Formula XVII.

In step (2a) of Reaction Scheme II, the acetamine protecting group is removed under acidic conditions to provide the compound of Formula XVIII, which is a subgenus of Formula I. The reaction can be conducted according to the procedure described in step (2).

Reaction Scheme II

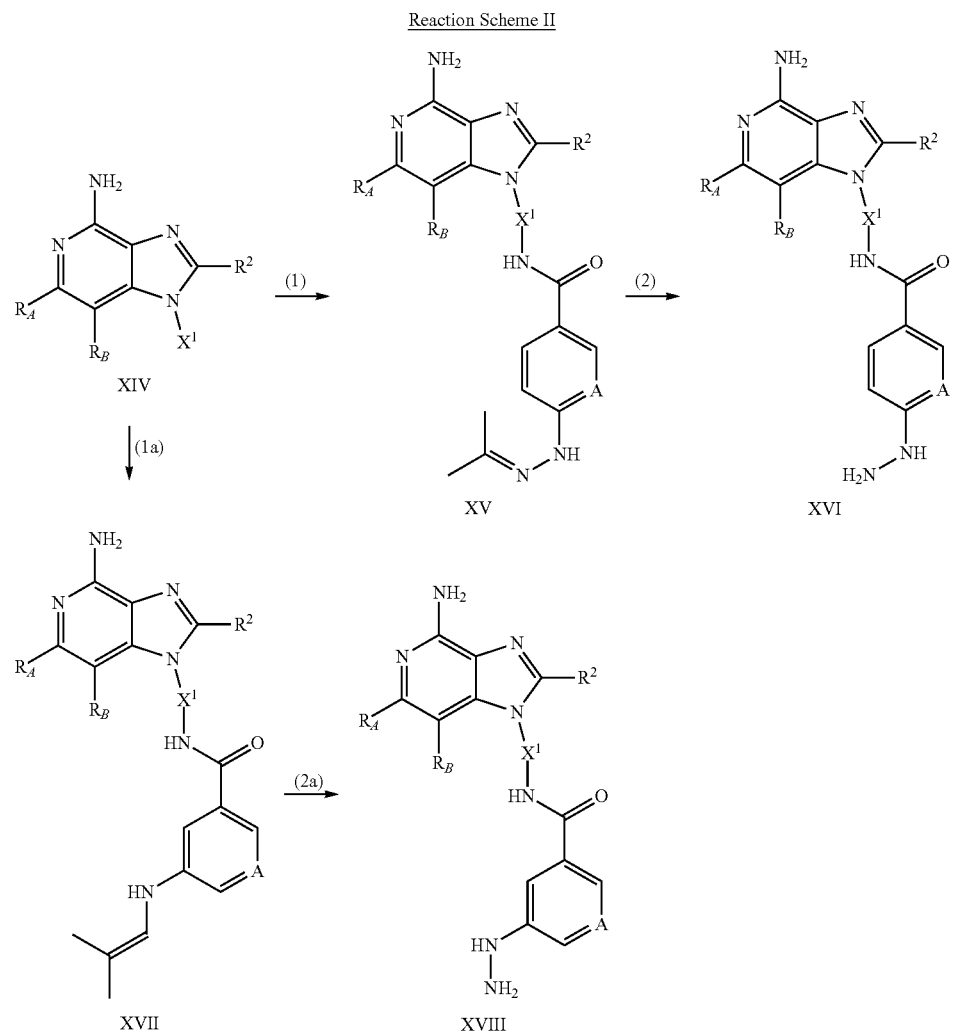

In some embodiments, IRM compounds useful for making the conjugates of the present invention can be prepared according to the method of Reaction Scheme III wherein $R_2$, $R_A$, $R_B$, and $X^1$ are as defined above.

In step (1) of Reaction Scheme III, a compound of Formula XIV is reacted with at least two equivalents of succinic anhydride. The reaction can be carried out in a suitable solvent such as DMF at an elevated temperature such as 100° C. The product of Formula XIX, or a pharmaceutically acceptable salt thereof, can be isolated using conventional methods.

In step (2) of Reaction Scheme III, the acid group on a compound of Formula XIX is activated with a carbodiimide reagent, for example, 1-(3-dimethylaminopropyl)-3-ethyl-carbodiimide hydrochloride (EDC), in the presence of tert-butylcarbazate. The reaction can be carried out in a suitable solvent such as dichloromethane, optionally in the presence of a base such as triethylamine or a catalyst such as N,N-dimethylpyridin-4-amine (DMAP). The protecting group in the intermediate product can be removed by treatment with an excess of an amine such as, for example, ethylene diamine, in a suitable solvent such as dichloromethane to provide the product of Formula XX. Compounds of Formula XX, or a pharmaceutically acceptable salt thereof, can be isolated using conventional methods.

In step (3) of Reaction Scheme III, the tert-butoxycarbonyl (BOC) group in a compound of Formula XX is removed under acidic conditions to provide a functionalized IRM of Formula XXI, which is a subgenus of Formula I. The reaction can be carried out by treating a solution of a compound of Formula XX in a suitable solvent such as dichloromethane with an acid such as trifluoroacetic acid at ambient temperature. The product of Formula XXI, or a pharmaceutically acceptable salt thereof, can be isolated using conventional methods. Some compounds of Formula XXI are known, for example, N-{2-[4-Amino-2-(ethoxymethyl)-1H-imidazo[4,5-c]quinolin-1-yl]-1,1-dimethylethyl}-4-hydrazino-4-oxobutanamide is IRM 5 in U.S. Pat. Appl. Pub. No. 2009/0035323 (Stoermer et al.).

Reaction Scheme III

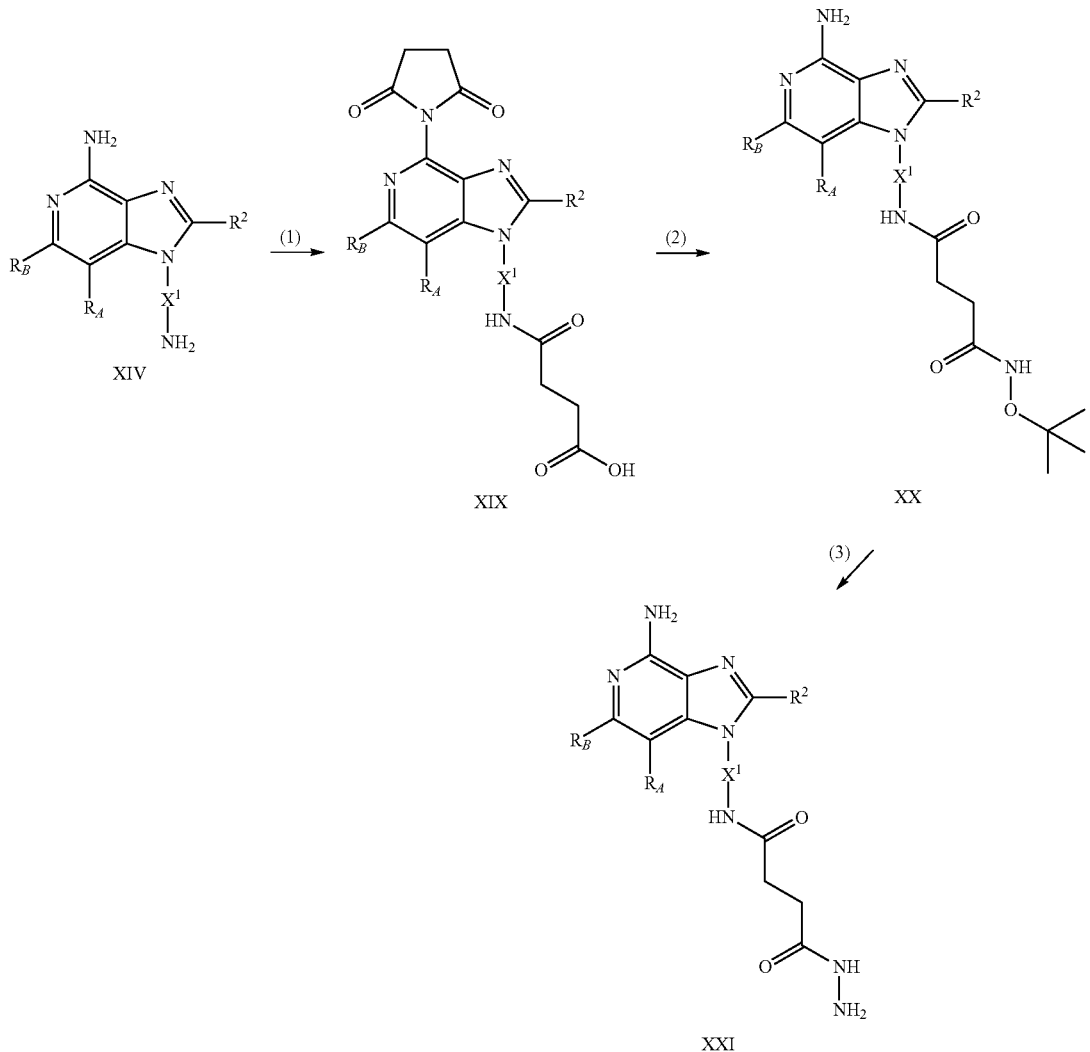

In some embodiments, IRM compounds useful for preparing the conjugates of the present invention can be prepared according to the methods described in Reaction Schemes II and III using compounds of Formulas XXII, XXIII, XXIV, XXV, XXVI, or XXVII wherein $R_1$, $R_2$, $R_A$, $R_B$, $X^1$, A, and Z are as described above, in lieu of a compound of Formula XIV. In some embodiments of Formulas XXII, XXIII, XXIV, and XXVI, the —Z—X—NH$_2$ or —X—NH$_2$ groups are attached at the 7 position or the 8 position.

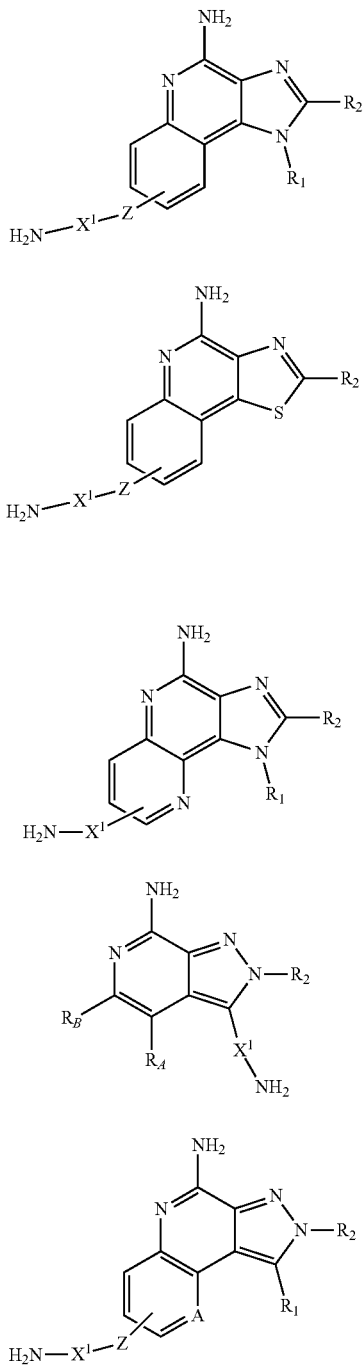

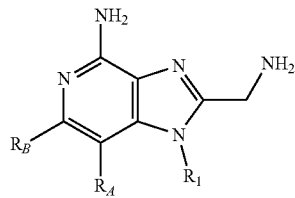

Many compounds of Formulas XXII, XXIII, XXIV, XXV, XXVI, and XXVII are known; others can be prepared using known synthetic methods. See for example, U.S. Patent Application Publication No. 2004/0147543; International Publication Nos. WO2005/020999, WO2005/032484, WO2005/079195, WO2006/009826, WO2006/038923, WO2006/093514, and WO2005/123079.

Linkers of the present invention and/or useful for making the modified antigens or conjugates of the present invention may be prepared, for example, according to the method of Reaction Scheme IV, wherein p, LG, R', R", and A are as defined above.

In step (1) of Reaction Scheme IV, an amino acid of Formula XXVIII is reacted with an activated ester of formyl benzoic acid or formyl nicotinic acid to provide a formyl benzamide or formyl nicotinamide represented by Formula XXIX. The activated ester can be, for example, an N-hydroxysuccinimide ester, sulfo-N-hydroxysuccinimide ester or a salt thereof, 4-nitrophenyl ester, pentafluorophenyl ester, tetrafluorophenyl ester, or N-hydroxybenzotriazole ester. Some of these compounds (e.g., N-succinimidyl-4-formylbenzoate) are commercially available. Others can be prepared by conventional methods. Some compounds of Formula XXVIII are commercially available (e.g., carboxy-PEG-amine compounds available from Thermo Scientific, Rockford, Ill., wherein R" is a bond and R' is ethylene), and others can be prepared by known methods (e.g., Riener, C. K., et al. *Anal. Chim. Acta,* 497, pp. 101-114 (2003) where R" is propoxy and R' includes a propyl group). Formation of the amide can be carried out in a suitable solvent such as dichloromethane or chloroform in the presence of a base such as triethylamine and optionally catalytic DMAP. The reaction can be carried out at room temperature, and the product of Formula XXIX can be carried out by conventional methods.

In step (2) of Reaction Scheme IV, the carboxylic acid of Formula XXIX is converted in some embodiments to an activated ester to provide the linker of Formula XXX. In some embodiments, LG in the activated ester of Formula XXX is selected from the group consisting of N-succinimidyloxy, p-nitrophenoxy, pentafluorophenoxy, tetrafluorophenoxy, N-benzotriazolyloxy, and sulfo-N-succinimidyloxy or a sodium salt thereof. The reaction may be carried out by reacting the compound of Formula XXIX with N,N,N',N'-tetramethyl-O—(N-succinimidyl)uronium tetrafluoroborate (TSTU) in a suitable solvent or solvent combination such as N,N-dimethylformamide and pyridine. The reaction can be carried out at room temperature. Alternatively, the compound of Formula XXIX can be treated with, for example, N-hydroxysuccinimide, sulfo-N-hydroxysuccinimide or a salt thereof (e., a sodium salt), 4-nitrophenol, pentafluorophenol, tetrafluorophenol, or N-hydroxybenzotriazole in the presence of a standard coupling agent such as DCC or EDC in a suitable solvent such as dichloromethane or pyridine. The product of Formula XXX can be isolated by conventional methods.

In some embodiments, step (2) of Reaction Scheme IV involves converting the carboxylic acid of Formula XXIX to an acid chloride, acid bromide, or acid iodide to provide a linker of Formula XXX in which LG is —Cl, —Br, or —I.

The reaction can be carried out using conventional methods, for example, by treating the carboxylic acid with thionyl chloride, phosphorous trichloride, phosphorous pentachloride, oxalyl chloride, or cyanuric chloride in a suitable solvent.

Reaction Scheme IV

NH$_2$—R''—(CH$_2$CH$_2$O)$_p$—R'—C(O)—OH $\xrightarrow{(1)}$

XXVIII

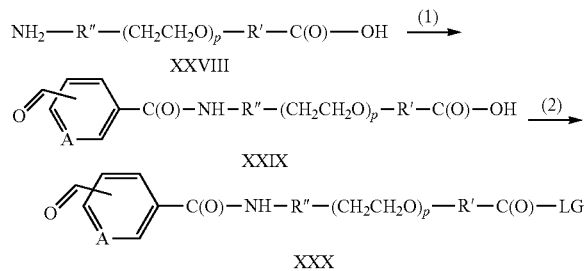

XXIX

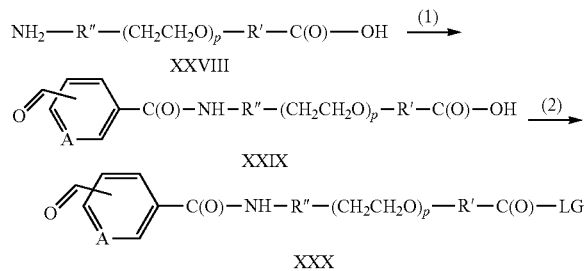

XXX

In some embodiments, linkers according to the present invention and/or useful for making the conjugates of the present invention can be prepared according to Reaction Scheme V, wherein p, LG, R', R'', and A are as defined above, E' is a bromoacetyl, chloroacetyl, iodoacetyl, or isocyanate.

In some embodiments, step (1) of Reaction Scheme V is useful for converting an acid chloride of Formula XXX where LG is —Cl into a compound of Formula XXXI, wherein E' is bromoacetyl, chloroacetyl, or iodoacetyl. The reaction can be carried out using conventional methods such as treating the acid chloride with diazomethane to provide a diazoacetyl compound, which can then be treated with hydrobromic acid or hydrochloric acid, for example, to provide the chloroacetyl or bromoacetyl group.

In other embodiments, step (1) of Reaction Scheme V is useful for converting an acid chloride of Formula XXX where LG is —Cl into a primary amide by reaction with ammonia using conventional methods. A primary amide can then undergo the Hofmann rearrangement in the presence of a bromide source such as N-bromosuccinimide to provide a compound of Formula XXXI where E' is an isocyanate group.

In some embodiments, step (2) of Reaction Scheme V is useful for preparing a compound of Formula XXXII where E is a maleimide, and Ra is alkylene that is interrupted by an amide group. For example, an activated carboxylic acid of Formula XXX can be treated with aminopropylmaleimide or aminoethylmaleimide, which are typically commercially available in salt form, using conventional methods.

In other embodiments, step (2) of Reaction Scheme V is useful for preparing a compound of Formula XXXII where E is a chloroformate, —OC(O)—O—CH(Cl)CCl$_3$, —OC(O)—O—(4-nitrophenyl), or succinimidyl carbonate, and R$^a$ is alkylene that is interrupted by an amide group. Such compounds can be prepared, for example, by treating an activated carboxylic acid of Formula XXX with an amino alcohol (e.g., aminoethanol or aminopropanol), and the resulting alcohol can be treated with the appropriate carbonic acid derivative to provide the desired linker.

Reaction Scheme V

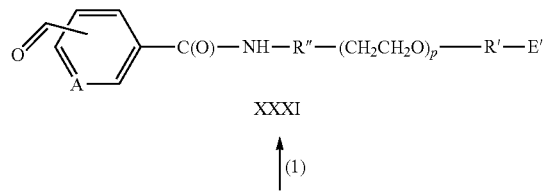

XXXI $\downarrow$(1)

-continued

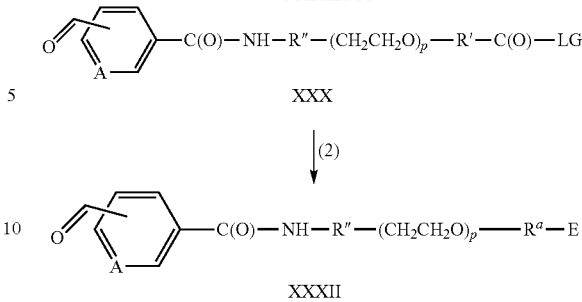

XXX $\downarrow$(2)

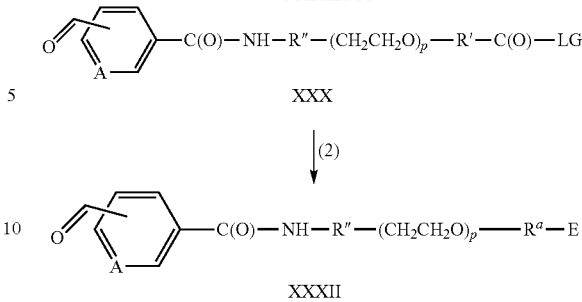

XXXII

Linkers useful for making conjugates of the present invention can also be made using modifications of Reaction Schemes IV and V that would be apparent to a person skilled in the art. Linkers useful for making conjugates of the present invention can also be made by beginning with a commercially available poly(ethylene glycol) diamine instead of an amino acid of Formula XXVIII. One terminus of the diamine may be reacted according to the methods of step (1) of Reaction Scheme IV, above, and the other may be treated with known heterobifunctional crosslinkers such as sulfo-N-succinimidyl 4-(maleimidomethyl)cyclohexane-1-carboxylate, N-(gamma-maleimidobutyryloxy)sulfosuccinimide ester, N-succinimidyl-3-(bromoacetamido)propionate, and 4-succinimdiyloxycarbonylmethyl-alpha-(2-pyridyldithio)toluene, which are commercially available, for example, from Thermo Scientific.

Modified antigens (e.g., antigens modified with any of the linkers described above in any of their embodiments) can be prepared according to a variety of methods. Typically, the antigen has a reactive functional group that allows a reaction with the linker. For example, an antigen may have one or more (e.g., typically multiple) terminal amino groups from lysine residues that may be reactive, for example, with an E group (e.g., activated carboxylic acid group) on the linker. It will be appreciated by those of skill in the art that in biomolecules such as proteins that contain multiple amino groups (i.e., lysines), as many amino groups as desired may be reacted with linkers. The degree of modification can be controlled by the number of mole equivalents of linking compounds used. In other embodiments, an antigen may have one or more (e.g., typically multiple) terminal thiol groups from cysteine residues that may be reactive, for example, with an E group (e.g., maleimide or disulfide group) on the linker. Again, the degree of modification can be controlled by the number of mole equivalents of linking compounds used.

The reaction of an antigen and a linker can be carried out in an appropriate buffered solution (e.g., in a phosphate buffer at a pH in a range from 7.2 to 7.5). The linker can be dissolved in an appropriate polar solvent (e.g., DMSO or DMF) and combined with the buffered solution containing the antigen. The reaction can conveniently be carried out at room temperature. In some embodiments, the linker is a compound represented by formula:

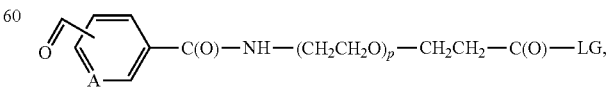

wherein A, p, and LG are as defined above in any of their embodiments, and the modified antigen has at least one segment represented by formula:

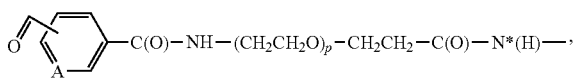

wherein A and p are as defined above in any of their embodiments, and the nitrogen atom indicated by N* is covalently bonded to the antigen.

In some embodiments of making a conjugate according to the present invention, the hydrazine- or hydrazide-substituted immune response modifier can be dissolved in an appropriate polar solvent (e.g., DMSO, DMF) and combined with an appropriate buffered solution of the antigen modified with the linker as described above. In some embodiments, the hydrazine or hydrazide functional group may be protected with an acid-labile protected amino group, for example, forming an imine (e.g., isopropylidenehydrazino group as shown in Formulas XV and XVII in Reaction Scheme II above) or a carbamate (e.g., tert-butoxycarbonylamino) In these embodiments, an acidic buffered solution (e.g., with a pH in a range from 4.7 to 6.2) can effect the deprotection of the amino group and allow reaction with the aldehyde-bearing antigen at the same time. The reaction is typically carried out at room temperature. Accordingly, in some embodiments of the method of making a conjugate according to the present invention, the method comprises combining a protected hydrazine- or protected hydrazide-substituted immune response modifier; an aldehyde-modified antigen as described in any of the above embodiments, and a carrier under conditions where the protected amino group is deprotected and the conjugate is formed.

When an aromatic, hydrazine- or hydrazide-substituted immune response modifier is reacted with an antigen modified by the linkers disclosed herein, the reaction of the aromatic aldehyde group with the aromatic hydrazine or hydrazide can conveniently be followed using a UV spectrophotometric assay. The bis-aromatic hydrazone bond that is formed provides a distinctive chromophore with a maximal absorbance a 354 nm and a molar extinction coefficient equal to 29,000. The number of moles of a compound of IRM incorporated into antigen can be calculated by dividing the measured absorbance of the conjugate at 354 nm by the molar extinction coefficient of 29,000 as demonstrated in the Examples, below.

To promote solubility and stability in the reaction to provide conjugates disclosed herein, various additives may be useful in the reaction mixture depending on the properties of the selected antigen or protein. For example, glycerol and/or surfactants (e.g., polysorbate 80) can be useful for promoting solubility and stability. Conveniently, since the linkers according to and/or useful for practicing the present invention include a poly(ethylene glycol) segment, they promote solubility and stability of a protein without the addition of glycerol and/or surfactants. To promote reaction efficiency, catalysts (e.g., aniline) may be added in effective amounts (e.g., up to 200 mM). Advantageously, however, the hydrazone bonds in the conjugates according to the present invention can be made without catalysis.

Conjugates of the invention can also be prepared using the synthetic routes described in the EXAMPLES below.

In some embodiments, the antigen is a protein. Exemplary proteins that may be useful antigens in conjugates of the invention include hemagglutinin from H1N1 $PR_8$, hepatitis B surface antigen, Leishmania antigen, respiratory syncytial virus secretory protein F, malaria surface antigen, prostatic alkaline phosphatase prostate cancer antigen, and M phase phosphoprotein 1 bladder cancer antigen.

The optimum reaction conditions may vary according to varying protein characteristics including isoelectric point, grand average of hydropathy, the instability index (an estimate of the stability of protein in a test tube), the elative volume occupied by aliphatic side chains (alanine, valine, isoleucine, and leucine), which is regarded as a positive factor for the increase of thermostability of globular proteins, the number of anionic residues, and the number of cationic residues. Such characteristics are known for a variety of proteins.

The stability of proteins and maintenance of their native conformations are subject to a combination of hydrophobic interactions within their interior domains and the hydrogen bonding and charge interactions on the exterior surface of their structure. As these surface interactions are altered by modification with reagents such as linkers according to and/or using for practicing the present invention, the native conformation of the protein may be altered. To provide the conjugate (i.e., the reaction product of the IRM, linker, and a protein), a ratio of the linker to the protein can be varied such that the stability of the protein and its native conformation is maintained In some embodiments, a ratio of the linker to the protein is in a range from 30:1 to 1:3. In some embodiments, a ratio of the linker to the protein is in a range from 20:1 to 1:2. In some embodiments, a ratio of the linker to the protein is in a range from 10:1 to 1:1. The number of equivalents of the immune response modifier may be the same or similar to the number of equivalents of the linker used in some embodiments. In some embodiments, a ratio of the conjugated IRM to the protein is in a range from 30:1 to 1:6. In some embodiments, a ratio of the conjugated IRM to the protein is in a range from 20:1 to 1:5. In some embodiments, a ratio of the conjugated IRM to the protein is in a range from 10:1 to 1:1.

As shown in the EXAMPLES below, conjugates prepared from a linker disclosed herein provide a higher amount of total conjugated protein, a higher amount of soluble conjugated protein, and a higher percent yield of conjugated protein than conjugates prepared from a conventional heterobifunctional linker: succinimidyl 4-formylbenzoate (SFB).

Pharmaceutical Compositions and Methods

A conjugate of the present invention may be administered in a pharmaceutical composition disclosed herein in any suitable manner (e.g., non-parenterally or parenterally). As used herein, non-parenterally refers to administration through the digestive tract, including by oral ingestion. Parenterally refers to administration other than through the digestive tract which would include nasal (e.g., transmucosally by inhalation), topical, ophthalmic, and buccal adminstration, but in practice usually refers to injection (e.g., intravenous, intramuscular, subcutaneous, intratumoral, or transdermal) using, for example, conventional needle injection, injection using a microneedle array, or any other known method of injection.

A conjugate of the present invention may be provided in any pharmaceutical composition suitable for administration to a subject and may be present in the pharmaceutical composition in any suitable form (e.g., a solution, a suspension, an emulsion, or any form of mixture). The pharmaceutical composition may be formulated with any pharmaceutically acceptable excipient, carrier, or vehicle. The pharmaceutical composition may further include one or more additives including skin penetration enhancers, colorants, fragrances, flavorings, moisturizers, thickeners, suspending agents, surfactants, and dispersing agents.

In addition to antigens specifically described above and below, the pharmaceutical compositions and methods of the present disclosure can include other additional active agents, e.g., in admixture or administered separately. Such additional agents can include a chemotherapeutic agent, a cytotoxoid agent, an antibody, an antiviral agent, a cytokine, a tumor necrosis factor receptor (TNFR) agonist, or an additional immune response modifier. TNFR agonists that may be delivered in conjunction with a conjugate of the present invention (in some embodiments, the conjugate of Formula II) include CD40 receptor agonists, such as disclosed in application U.S. Pat. Appl. Pub. No. 2004/0141950 (Noelle et al.). Other active ingredients for use in combination with an IRM preparation of the present invention include those disclosed in, e.g., U.S. Pat. Appl. Pub. No. 2003/0139364 (Krieg et al.).

Conjugates according to the present disclosure can induce the production of INF-α and TNF-α in human cells. The ability to induce INF-α and TNF-α production indicates that the conjugates of the invention can modulate the immune response in a number of different ways, rendering it useful in the treatment of a variety of disorders. Other cytokines whose production may be induced by the administration of the compounds and conjugates disclosed herein generally include Type I interferons (e.g., INF-α), IL-1, IL-6, IL-8, IL-10, IL-12, MIP-1, MCP-1, and a variety of other cytokines. Among other effects, these and other cytokines inhibit virus production and tumor cell growth, making the conjugates of the present invention useful in the treatment of viral diseases and neoplastic diseases. For example, tumor necrosis factor, interferons, or interleukins have been shown to stimulate a rapid release of certain monocyte/macrophage-derived cytokines and are also capable of stimulating B cells to secrete antibodies which play an important role in antiviral and antitumor activities.

In addition to the ability to induce the production of cytokines, the conjugates described herein may affect other aspects of the innate immune response. For example, natural killer cell activity may be stimulated, an effect that may be due to cytokine induction. IRM activity of the conjugate of the present invention also may include activating macrophages, which in turn stimulate secretion of nitric oxide and the production of additional cytokines. IRM activity of the conjugate of the present invention also may include inducing cytokine production by T cells, activating T cells specific to an antigen, and/or activating dendritic cells. Further, IRM activity of the conjugate may include proliferation and differentiation of B-lymphocytes. IRM activity of the conjugate also may affect the acquired immune response. For example, IRM activity can include inducing the production of the T helper type 1 ($T_H1$) cytokine IFN-γ and/or inhibiting the production of the T helper type 2 ($T_H2$) cytokines IL-4, IL-5 and/or IL-13.

A conjugate prepared from an IRM, a linker described herein, and hemagglutinin 1 (HA) can demonstrate a potent vaccine adjuvant effect with a strong $T_H1$ biased immune response indicated by the increased ratio of HA specific IgG2a to HA specific IgG1 antibody. Such responses are typically accompanied by HA stimulation of T cell interferon gamma production and the generation of cell mediated, cytotoxic T cell immunity towards HA expressing cells, as well as other vaccine antigens. Such antigens may be those associated with and intended for treatment of viral and bacterial infectious diseases as well as various cancers.

Accordingly, the invention provides a method of inducing cytokine biosynthesis in an animal comprising administering an effective amount of the conjugate according to the present invention (or made according to the present invention) to the animal In some embodiments of the conjugate of the present invention, the antigen is a vaccine, and methods according to the invention include a method of vaccinating an animal comprising administering to the animal a conjugate according to and/or made according to the present disclosure. Vaccines include any material administered to raise either humoral and/or cell mediated immune response, such as live or attenuated viral and bacterial immunogens and inactivated viral, tumor-derived, protozoal, organism-derived, fungal, and bacterial immunogens, toxoids, toxins, polysaccharides, proteins, glycoproteins, peptides, cellular vaccines (e.g., using dendritic cells), DNA vaccines, recombinant proteins, glycoproteins, and peptides. Exemplary vaccines include vaccines for cancer, BCG, cholera, plague, typhoid, hepatitis A, B, and C, influenza A and B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, severe acute respiratory syndrome (SARS), anthrax, and yellow fever. See also, e.g., vaccines disclosed in International Publication No. WO 02/24225 (Thomsen et al.).

The methods of the present invention may be performed on any suitable subject. Suitable subjects include animals such as humans, non-human primates, rodents, dogs, cats, horses, pigs, sheep, goats, or cows.

The animal to which the conjugate is administered for induction of cytokine biosynthesis or for vaccination may have a disease (e.g., a viral or neoplastic disease), and administration of the compound may provide therapeutic treatment. Also, the conjugate may be administered to the animal before the animal acquires the disease so that administration of the conjugate may provide a prophylactic treatment. For example, a conjugate may be made from an IRM, a linker, and an HIV antigen and may provide therapeutic and/or prophylactic treatment for HIV. In another example, a conjugate may be made from an IRM, a linker, and a tumor-associated antigen and may provide therapeutic and/or prophylactic treatment against a tumor associated with the antigen.

Exemplary conditions that may be treated by administering an IRM conjugate include:

(a) viral diseases such as diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases such as chlamydia, fungal diseases (e.g., candidiasis, aspergillosis, histoplasmosis, or cryptococcal meningitis), or parasitic diseases (e.g., malaria, pneumocystis carnii pneumonia, leishmaniasis, cryptosporidiosis, toxoplasmosis, and trypanosome infection);

(d) neoplastic diseases such as intraepithelial neoplasias, cervical dysplasia, actinic keratosis, basal cell carcinoma, squamous cell carcinoma, renal cell carcinoma, Kaposi's sarcoma, melanoma, leukemias (e.g., myelogenous leukemia, chronic lymphocytic leukemia, multiple myeloma, non-Hodgkin's lymphoma, cutaneous T-cell lymphoma, B-cell lymphoma, and hairy cell leukemia), breast cancer, lung cancer, prostate cancer, colon cancer, and other cancers;

(e) $T_H2$-mediated, atopic diseases such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, and alopecia areata; and (g) diseases associated with wound repair such as inhibition of keloid formation and other types of scarring (e.g., enhancing wound healing, including chronic wounds).

IRM conjugates also may be useful to individuals having compromised immune function. For example, certain conjugates may be useful for treating the opportunistic infections and tumors that occur after suppression of cell mediated immunity in, for example, transplant patients, cancer patients, and HIV patients.

It will be understood that in the treatment of the diseases mentioned above, for example, the conjugate disclosed herein can be used in combination with other therapies such as the active agents mentioned above and other procedures (e.g., chemoablation, laser ablation, cryotherapy, and surgical excision).

An amount of a conjugate effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-1O and IL-12 that is increased over a background level of such cytokines. The precise amount will vary according to factors known in the art but is expected to be a dose of about 100 nanograms per kilograms (ng/kg) to about 50 milligrams per kilogram (mg/kg), in some embodiments about 10 micrograms per kilogram (μg/kg) to about 5 mg/kg, about 100 μg/kg to about 1 mg/kg, or about 0.01 mg/m$^2$ to about 10 mg/m$^2$. Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184. An amount effective to treat or inhibit a viral infection, for example, is an amount that will cause a reduction in one or more of the manifestations of viral infection, such as viral lesions, viral load, rate of virus production, and mortality as compared to untreated control animals and may include any of the aforementioned doses. An amount of a conjugate or pharmaceutical composition effective to treat a neoplastic condition is an amount that will cause a reduction in tumor size or in the number of tumor foci and may include any of the aforementioned doses.

The composition of a formulation suitable for practicing the invention, the precise amount of a conjugate effective for methods according to the present invention, and the dosing regimen, for example, will vary according to factors known in the art including the nature of the carrier, the state of the subject's immune system (e.g., suppressed, compromised, stimulated), the method of administering the conjugate, and the species to which the formulation is being administered. Accordingly, it is not practical to set forth generally the composition of a formulation that includes a conjugate according to the present disclosure, an amount of the conjugate that constitutes an effective amount, or a dosing regimen that is effective for all possible applications. Those of ordinary skill in the art, however, can readily determine appropriate formulations, amounts of the conjugate, and dosing regimen with due consideration of such factors.

In some embodiments, the methods of the present invention include administering a conjugate to a subject in a formulation, for example, having a concentration of the compound from about 0.0001% to about 20% (unless otherwise indicated, all percentages provided herein are weight/weight with respect to the total formulation), although in some embodiments the conjugate may be administered using a formulation that provides the compound in a concentration outside of this range. In some embodiments, the method includes administering to a subject a formulation that includes from about 0.01% to about 1% of the conjugate, for example, a formulation that includes about 0.1% to about 0.5% compound of the conjugate.

In some embodiments of the methods disclosed herein, the conjugate may be administered, for example, from a single dose to multiple doses per week, although in some embodiments the methods of the present invention may be performed by administering the conjugate at a frequency outside this range. In some embodiments, the conjugate may be administered from about once per month to about five times per week. In some embodiments, the conjugate is administered once per week.

The conjugate may also be used as a booster following initial immunization with a DNA or RNA vaccine encoding, whole or in part, the same antigen.

Some Embodiments of the Invention

In a first embodiment, the present invention provides a conjugate comprising a reaction product of:

a hydrazine- or hydrazide-substituted immune response modifier;

a linker represented by formula:

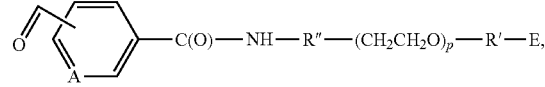

wherein A is CH or N, p is in a range from 1 to 50, R" is a bond or -alkylene-O—, R' is alkylene that is optionally interrupted or terminated with one or more amide or ether groups, and E is an amine- or thiol-reactive group; and an antigen.

In a second embodiment, the present invention provides the conjugate of the first embodiment, wherein the hydrazine- or hydrazide-substituted immune response modifier is hydrazine-substituted and comprises an aromatic ring to which the hydrazine is bonded.

In a third embodiment, the present invention provides the conjugate of the first or second embodiment, wherein the hydrazine- or hydrazide-substituted immune response modifier is a hydrazine-substituted imidazoquinoline amine, imidazonaphthyridine amine, pyrazoloquinoline amine, pyrazolonaphthyridine amine, or a thiazoloquinoline amine.

In a fourth embodiment, the present invention provides the conjugate of any one of the first to third embodiments, wherein E is selected from the group consisting of maleimide, vinylsulfone, acrylamide, pyridyldisulfide, methyl sulfonyl disulfide, N-hydroxysuccinimide ester, sulfo-N-hydroxysuccinimide ester or a salt thereof, 4-nitrophenyl ester, acid chloride, acid bromide, acid anhydride, pentafluorophenyl ester, tetrafluorophenyl ester, N-hydroxybenzotriazole ester, iodoacetyl, bromoacetyl, chloroacetyl, succinimidyl carbonate, chloroformate, —OC(O)—O—CH(Cl)CCl$_3$, —OC(O)—O-(4-nitrophenyl), isocyanate, and thioisocyanate.

In a fifth embodiment, the present invention provides the conjugate of the fourth embodiment, wherein R' is alkylene having up to four carbon atoms, and E is an ester selected from the group consisting of N-hydroxysuccinimide ester, sulfo-N-hydroxysuccinimide ester or a salt thereof, 4-nitrophenyl ester, pentafluorophenyl ester, tetrafluorophenyl ester, and N-hydroxybenzotriazole ester.

In a sixth embodiment, the present invention provides the conjugate of any one of the first to fifth embodiments, wherein the antigen is a protein.

In a seventh embodiment, the present invention provides the conjugate of the sixth embodiment, wherein a ratio of the linker to the protein is in a range from 30:1 to 1:3.

In an eighth embodiment, the present invention provides the conjugate of any one of the first to fifth embodiments, wherein the antigen is a lipid.

In a ninth embodiment, the present invention provides the conjugate of any one of the first to eighth embodiments, wherein the hydrazine- or hydrazide-substituted immune response modifier is an imidazoquinoline amine, imidazonaphthyridine amine, pyrazoloquinoline amine, or pyrazolonaphthyridine amine, each of which is substituted at the 1-position.

In a tenth embodiment, the present invention provides a conjugate comprising:
an immune response modifier;
a linker represented by formula:

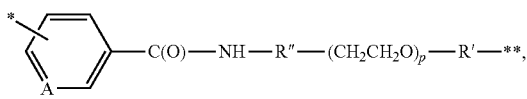

wherein A is CH or N, p is in a range from 1 to 50, R" is a bond or -alkylene-O—, and R' is a bond or alkylene that is optionally interrupted or terminated with one or more amide or ether groups; and an antigen, wherein the immune response modifier is covalently attached to the linker at * through a hydrazone functional group, and wherein the antigen is covalently attached to the linker at  through an amide, disulfide, urea, thiourea, carbamate, or a carbon-sulfur or carbon-nitrogen bond alpha to an amide or sulfone or directly attached to a succinimide ring. In some of these embodiments, the antigen is covalently attached to the linker at  through an amide functional group.

In an eleventh embodiment, the present invention provides the conjugate of the tenth embodiment, wherein immune response modifier is an imidazoquinoline amine, imidazonaphthyridine amine, pyrazoloquinoline amine, pyrazolonaphthyridine amine, or a thiazoloquinoline amine.

In a twelfth embodiment, the present invention provides the conjugate of the eleventh embodiment, wherein immune response modifier is an imidazoquinoline amine, imidazonaphthyridine amine, pyrazoloquinoline amine, or pyrazolonaphthyridine amine, and wherein the hydrazone functional group is located at the 1-position of the imidazoquinoline amine, imidazonaphthyridine amine, pyrazoloquinoline amine, or pyrazolonaphthyridine amine In a thirteenth embodiment, the present invention provides the conjugate of any one of the tenth through twelfth embodiments, wherein the antigen is a protein.

In a fourteenth embodiment, the present invention provides the conjugate of any one of the tenth through twelfth embodiments, wherein the antigen is a lipid.

In a fifteenth embodiment, the present invention provides the conjugate of the any one of the tenth to fourteenth embodiments, wherein the hydrazone functional group is bonded to an aromatic ring of the immune response modifier.

In a sixteenth embodiment, the present invention provides the conjugate of the any one of the first to fifteenth embodiments, wherein A is CH.

In a seventeenth embodiment, the present invention provides the conjugate of the any one of the first to fifteenth embodiments, wherein p is in a range from 2 to 16.

In an eighteenth embodiment, the present invention provides a method of making the conjugate of any one of the first to seventeenth embodiments, the method comprising:
combining an antigen with a linker to provide a modified antigen, wherein the linker is represented by formula:

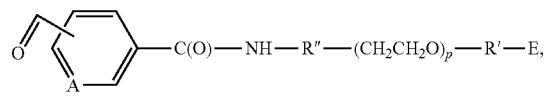

wherein A is CH or N, p is in a range from 1 to 50, R" is a bond or -alkylene-O—, R' is a bond or alkylene that is optionally interrupted or terminated with one or more amide or ether groups, and E is an amine- or thiol-reactive group; and combining the modified antigen with a hydrazine- or hydrazide-substituted immune response modifier to provide the conjugate.

In a nineteenth embodiment, the present invention provides a method of making a conjugate, the method comprising:
combining an antigen with a linker to provide a modified antigen, wherein the linker is represented by formula:

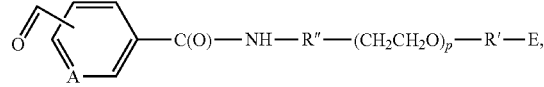

wherein A is CH or N, p is in a range from 1 to 50, R" is a bond or -alkylene-O—, R' is a bond or alkylene that is optionally interrupted or terminated with one or more amide or ether groups, and E is an amine- or thiol-reactive group; and combining the modified antigen with a hydrazine-or hydrazide-substituted immune response modifier to provide the conjugate.

In a twentieth embodiment, the present invention provides the method of the nineteenth embodiment, wherein the hydrazine- or hydrazide-substituted immune response modifier is hydrazine-substituted and comprises an aromatic ring to which the hydrazine is bonded.

In a twenty-first embodiment, the present invention provides the method of the nineteenth or twentieth embodiment, wherein the hydrazine- or hydrazide-substituted immune response modifier is a hydrazine-substituted imidazoquinoline amine, imidazonaphthyridine amine, pyrazoloquinoline amine, pyrazolonaphthyridine amine, or a thiazoloquinoline amine In a twenty-second embodiment, the present invention provides the method of any one of the nineteenth to twenty-first embodiments, wherein the hydrazine- or hydrazide-substituted immune response modifier is an imidazoquinoline amine, imidazonaphthyridine amine, pyrazoloquinoline amine, or pyrazolonaphthyridine amine, each of which is substituted at the 1-position.

In a twenty-third embodiment, the present invention provides the method of any one of the nineteenth to twenty-second embodiments, wherein E is selected from the group consisting of maleimide, vinylsulfone, acrylamide, pyridyldisulfide, methyl sulfonyl disulfide, N-hydroxysuccinimide ester, sulfo-N-hydroxysuccinimide ester or a salt thereof, 4-nitrophenyl ester, acid chloride, acid bromide, acid anhydride, pentafluorophenyl ester, tetrafluorophenyl ester, N-hydroxybenzotriazole ester, iodoacetyl, bromoacetyl, chloroacetyl, succinimidyl carbonate, chloroformate, —OC(O)—O—CH(Cl)CCl$_3$, —OC(O)—O-(4-nitrophenyl), isocyanate, and thioisocyanate.

In a twenty-fourth embodiment, the present invention provides the method of the twenty-third embodiment, wherein R' is alkylene having up to four carbon atoms, and E is an ester selected from the group consisting of N-hydroxysuccinimide ester, sulfo-N-hydroxysuccinimide ester or a salt thereof, 4-nitrophenyl ester, pentafluorophenyl ester, tetrafluorophenyl ester, and N-hydroxybenzotriazole ester.

In a twenty-fifth embodiment, the present invention provides the method of any one of the nineteenth to twenty-fourth embodiments, wherein the antigen is a protein.

In a twenty-sixth embodiment, the present invention provides the method of the twenty-fifth embodiment, wherein a ratio of the linker to the protein is in a range from 30:1 to 1:3.

In a twenty-seventh embodiment, the present invention provides the method of any one of the nineteenth to twenty-fourth embodiments, wherein the antigen is a lipid.

In a twenty-eighth embodiment, the present invention provides the method of the any one of the nineteenth to twenty-seventh embodiments, wherein A is CH.

In a twenty-ninth embodiment, the present invention provides the conjugate of the any one of the nineteenth to twenty-eighth embodiments, wherein p is in a range from 2 to 16.

In a thirtieth embodiment, the present invention provides a pharmaceutical composition comprising a pharmaceutically acceptable carrier and an effective amount of the conjugate of any one of the first to seventeenth embodiments.

In a thirty-first embodiment, the present invention provides a method of vaccinating an animal, the method comprising administering an effective amount of the conjugate of any one of the first to seventeenth embodiments or the pharmaceutical composition of the thirtieth embodiment to the animal In a thirty-second embodiment, the present invention provides a method of inducing cytokine biosynthesis in an animal, the method comprising administering an effective amount of the conjugate of any one of the first to seventeenth embodiments or the pharmaceutical composition of the thirtieth embodiment to the animal.

In a thirty-third embodiment, the present invention provides a conjugate or pharmaceutical composition for use in vaccinating an animal by administering an effective amount of the conjugate of any one of the first to seventeenth embodiments or the pharmaceutical composition of the thirtieth embodiment to the animal.

In a thirty-fourth embodiment, the present invention provides a conjugate or pharmaceutical composition for use in stimulating an antigen-specific response in an animal by administering an effective amount of the conjugate of any one of the first to seventeenth embodiments or the pharmaceutical composition of the thirtieth embodiment to the animal.

In a thirty-fifth embodiment, the present invention provides a conjugate or pharmaceutical composition for use inducing cytokine biosynthesis in an animal by administering an effective amount of the conjugate of any one of the first to seventeenth embodiments or the pharmaceutical composition of the thirtieth embodiment to the animal In a thirty-sixth embodiment, the present invention provides a compound represented by formula:

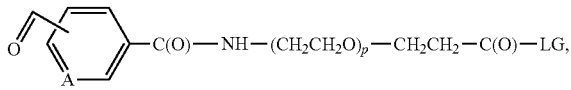

wherein A is CH or N, p is in a range from 1 to 50, and LG is a group that can be displaced by an amine In a thirty-seventh embodiment, the present invention provides the compound of the thirty-sixth embodiment, wherein LG is selected from the group consisting of N-succinimidyloxy, p-nitrophenoxy, pentafluorophenoxy, N-benzotriazolyloxy, and sulfo-N-succinimidyloxy or a sodium salt thereof.

In a thirty-eighth embodiment, the present invention provides the compound of the thirty-sixth or thirty-seventh embodiment, wherein p is in a range from 2 to 16.

In a thirty-ninth embodiment, the present invention provides a modified antigen having at least one segment represented by formula:

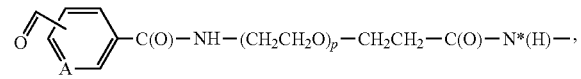

wherein A is CH or N, p is in a range from 1 to 50, and the nitrogen atom indicated by N* is covalently bonded to the antigen.

In a fortieth embodiment, the present invention provides the modified antigen of the thirty-ninth embodiment, wherein p is in a range from 2 to 16.

In a forty-first embodiment, the present invention provides the modified antigen of the thirty-ninth or fourtieth embodiment, wherein the antigen is a protein.

In a forty-second embodiment, the present invention provides the conjugate or method of any one of the first to twenty-ninth embodiments except the 9, 12, and 22 embodiments, wherein the immune response modifier is a imidazoquinoline amine, imidazonaphthyridine amine, pyrazoloquinoline amine, pyrazolonaphthyridine amine, or a thiazoloquinoline amine, each of which is conjugated through the 7-position.

Embodiments of this invention are further illustrated by the following non-limiting examples, but the particular materials and amounts thereof recited in these examples, as well as other conditions and details, should not be construed to unduly limit this invention.

EXAMPLES

Example 1

Compound A

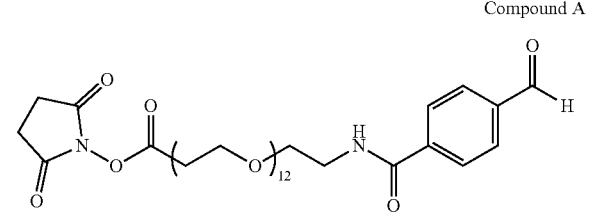

Part A

CA(PEG)12 (formula of $H_2N-CH_2CH_2-(OCH_2CH_2)_{12}-CO_2H$; MW=617.7; obtained from Thermo Scientific, Rockford, Ill., 115 mg) dissolved in dry dichloromethane (5 mL), N-Succinimidyl-4-formylbenzoate (52 mg dissolved in dry dichloromethane (0.5 mL) obtained from EMD Chemicals, Gibbstown, N.J.), dry triethylamine (52 µL), and a catalytic amount of DMAP were combined under an atmosphere of nitrogen. The reaction was stirred for 3 hours and then diluted with dichloromethane (25 mL). The organic fraction was washed with 0.1 M sodium phosphate (2×10 mL) followed by brine. The organic fraction was dried over sodium sulfate, filtered, and concentrated under reduced pressure. The aqueous wash fractions were combined and extracted with several portions of dichloromethane. The aqueous fraction was then acidified to pH ~2 with dilute hydrochloric acid and extracted with two additional portions of dichloromethane. The organic extracts were combined, dried over sodium sulfate, filtered, and concentrated under reduced pressure. The resulting material was combined with the material obtained from the first extraction and purified using a small column of silica gel. Elution with 10-25% methanol/chloroform, saturated with water, yielded 58 mg of the amide product as a colorless solid. $^1$H NMR (chloroform-d, 500 MHz) δ 10.08 (s, 1H), 8.00 (d, J=8.2 Hz, 2H), 7.95 (d, J=8.4 Hz, 2H), 7.19 (m, 1H), 3.77 (t, J=6.1 Hz, 2H), 3.70-3.60 (m, 48H), 2.60 (t, J=6.1 Hz, 2H).

Part B

The material from Part A was dissolved in dry N,N-dimethylformamide (0.5 mL) and dry pyridine (0.5 mL). O—(N-Succinimidyl)-1,1,3,3-tetramethyluronium tetrafluoroborate (TSTU; 46 mg; available from Sigma-Aldrich, St. Louis, Mo. was added and the reaction was stirred under a nitrogen atmosphere for 3 hours. Most of the solvent was removed under reduced pressure. The resulting material was dissolved in chloroform (25 mL) and methanol (5 mL) and placed in a separatory funnel. A buffer solution (10 mL of a solution of 0.10 M sodium chloride, 0.05 M sodium phosphate, 1.0 mM EDTA adjusted to pH 7.5 with sodium hydroxide) was added and the mixture was shaken for 2 minutes. The organic fraction was collected and washed sequentially with an additional portion of the buffer solution (10 mL), water (3×10 mL), and brine. The organic fraction was dried over sodium sulfate, filtered, and concentrated under reduced pressure to provide 55 mg of Compound A as a colorless syrup. $^1$H NMR (chloroform-d, 500 MHz) δ 10.08 (s, 1H), 7.99 (d, J=8.2 Hz, 2H), 7.95 (d, J=8.1 Hz, 2H), 7.10 (m, 1H), 3.85 (t, J=6.5 Hz, 2H), 3.70-3.60 (m, 48H), 2.90 (t, J=6.9 Hz, 2H) 2.84 (br s, 4H).

Example 2

Recombinant hemagglutinin 1 (HA) from H1N1 PR$_8$ was cloned, expressed in *E. coli*, and purified using standard procedures. The HA, molecular weight 32083.11 daltons, bearing 6 histidines at the C terminus, was placed in a pH 7.5, 0.1 M phosphate buffer, containing 0.15 M NaCl. Based on the molecular weight of the HA and the mass of protein, the molarity of the HA solution was established. Compound A dissolved in dimethyl sulfoxide (DMSO) was added to HA at a 10 fold molar excess. The solution was then incubated for 2 hours at room temperature. Compound A-modified HA (represented as HA-Compound A) was separated from free Compound A by use of a ZEBA spin column (Thermo Scientific, Rockford, Ill.) pre-equilibrated with pH 6.0, 0.1 M phosphate buffer containing 0.15 M NaCl. This step changed the HA-Compound A solution to pH 6.0 in preparation for the conjugation reaction.

Example 3

N-(4-{[4-Amino-2-butyl-1H-imidazo[4,5-c]quinolin-1-yl]oxy}butyl)-6-(N'-isopropylidenehydrazino)nicotinamide (prepared as described below) was dissolved in DMSO and added to the buffered HA-Compound A solution in a 10-fold molar excess. The acidic conditions of the reaction medium resulted in deprotection of the acetimine protecting group of N-(4-{[4-amino-2-butyl-1H-imidazo[4,5-c]quinolin-1-yl]oxy}butyl)-6-(N'-isopropylidenehydrazino)nicotinamide to form N-(4-{[4-amino-2-butyl-1H-imidazo[4,5-c]quinolin-1-yl]oxy}butyl)-6-hydazinonicotinamide in situ. The sample was incubated for 2 hours at room temperature. HA-Compound A covalently conjugated to N-(4-{[4-amino-2-butyl-1H-imidazo[4,5-c]quinolin-1-yl]oxy}butyl)-6-hydazinonicotinamide (represented as HA-Compound A-Compound 2) was separated from unconjugated components by use of a ZEBA spin column pre-equilibrated with Dulbecco's phosphate buffered saline (PBS) (Sigma-Aldrich, St. Louis, Mo.).

Preparation of N-(4-{[4-Amino-2-butyl-1H-imidazo[4,5-c]quinolin-1-yl]oxy}butyl)-6-(N'-isopropylidenehydrazino)nicotinamide (Compound 1) and N-(4-{[4-Amino-2-butyl-1H-imidazo[4,5-c]quinolin-1-yl]oxy}butyl)-6-hydazinonicotinamide Compound 2

(Compound 1)

(Compound 2)

Part A

A solution of valeric anhydride (6.03 g) and pyridine hydrochloride (0.198 g) in pyridine (8.28 g) was added to a solution of 3-amino-4-chloroquinoline (2.94 g) in pyridine (5.0 g) and the reaction was stirred at room temperature for 16 hours followed by heating at 60° C. for 3 hours. The reaction was concentrated under reduced pressure and sodium carbonate (15 mL of a 10% aqueous solution) was added. The reaction was stirred for 30 minutes and then filtered. The resulting solid was washed with water (60 mL) and dried under vacuum for 4 hours to provide 4.59 g of crude N-(4-chloroquinolin-3-yl)valeramide as brown flakes. The crude product was recrystallized from heptane (10 mL) and the recovered product was further purified by soxhlet extraction using refluxing heptane for 16 hours. The collection flask from the soxhlet extraction apparatus was cooled in a freezer for 2 hours. The resulting solid was collected by filtration and dried under vacuum to yield 2.00 g of N-(4-chloroquinolin-3-yl)valeramide as a white solid.

Part B

A solution of 4-amino-1-butanol (7.68 g) and pyridine (7.00 g) in dichloromethane (100 mL) was chilled in an ice bath and a solution of benzylchloroformate (14.37 g) in dichloromethane (100 mL) was slowly added with stirring over a period of thirty minutes. The ice bath was removed and the reaction was stirred for an additional 16 hours. Hydrochloric acid (1.2 M, 200 mL) was added and phases were separated. The organic phase was dried ($MgSO_4$), filtered and concentrated under reduced pressure. The resulting residue was recrystallized from toluene and dried under vacuum to provide 5.15 g of benzyl (4-hydroxybutyl)carbamate.

A solution of N-hydroxyphthalimide (3.36 g), benzyl (4-hydroxybutyl)carbamate (4.18 g) and triphenylphosphine (7.41 g) in dichloromethane (100 mL) was chilled in an ice bath and approximately two-thirds of a solution of diisopropylazodicarboxylate (DIAD, 5.68 g) in dichloromethane (50 mL) was slowly added with stirring. The internal temperature of the reaction was monitored and the addition of the DIAD solution was stopped when an exotherm could no longer be detected. The ice bath was removed and the reaction was allowed to warm to room temperature. The reaction was concentrated under reduced pressure and the resulting residue was dissolved in ethanol (200 proof, 100 mL). Hydrazine (1.98 g, 35% in water) was added and the reaction was stirred for 6 hours. The reaction was cooled in the freezer and the resulting solid was removed by filtration. The solid was washed with ethanol (50 mL). The combined filtrate was concentrated under reduced pressure and diethyl ether (100 mL) was added. Insoluble impurities were removed by filtration and 2.0 M HCl in ether (10 mL) was added to the solution. A precipitate formed immediately. The crude product was added to toluene (100 mL) and heated at reflux temperature for one hour. After cooling to room temperature, the solid product was recovered by filtration, washed with toluene, and dried under vacuum to yield 3.76 g of benzyl (4-aminooxybutyl)carbamate.

Part C

N-(4-Chloroquinolin-3-yl)valeramide (1.97 g), benzyl (4-aminooxybutyl)carbamate (2.99 g), triethylamine (0.89 g) and 2-propanol (40.69 g) were combined and heated at 80° C. for 3.5 hours. The reaction was cooled to room temperature, filtered, and the filtrate concentrated under reduced pressure. Dichloromethane (20 mL) was added to the resulting solid and the mixture was stirred for twenty minutes. Undissolved solid was removed by filtration and the filtrate was washed with two 10 mL portions of water that had been made slightly acidic by the addition of 20 drops of hydrochloric acid (1.2 M). The organic fraction was dried and concentrated under reduced pressure. The crude solid was recrystallized from tetrahydrofuran to provide 2.56 g of benzyl 4-{[2-butyl-1H-imidazo[4,5-c]quinolin-1-yl]oxy}butylcarbamate.

Part D

Benzyl4-{[2-butyl-1H-imidazo[4,5-c]quinolin-1-yl]oxy}butylcarbamate hydrochloride (10.05 g) was dissolved in dichloromethane (80 mL) and extracted with a solution of sodium carbonate (2.02 g) in 30 mL $H_2O$. The organic layer was cooled in an ice bath and a solution of m-chloroperbenzoic acid (5.93 g, 1.24 eq) dissolved in dichloromethane (30 mL) was slowly added. After 6 hr, ammonium hydroxide (10 mL of a 28-30% aqueous solution) was added to the reaction. A solution of benzenesulfonyl chloride (6.96 g) dissolved in 10 mL dichloromethane was slowly added with vigorous stirring. The cooling bath was removed and the reaction was stirred for an additional 12 hours. The reaction was diluted with water (100 mL) and the organic and aqueous fractions were separated. The aqueous fraction was extracted with dichloromethane (30 mL). The combined organic fractions were washed with two 90 mL portions of 5% sodium carbonate.

The dichloromethane solution was transferred to a distillation apparatus and 1-pentanol (50 mL) was added. This was warmed to 40° C. and the dichoromethane was removed under reduced pressure. Concentrated hydrochloric acid (50 mL) was then added and the reaction was stirred and heated to 80° C. After 11 hours, the solution was cooled to room temperature and diluted with water (100 mL). The aqueous fraction was separated from the 1-pentanol and the 1-pentanol was extracted with water (25 mL). The aqueous fractions were combined. 1-Pentanol (50 mL) was added to the combined aqueous fraction and this was cooled in an ice-bath. With vigorous stirring, solid sodium carbonate was added to bring the pH to 9-10. The mixture was transferred to a separatory funnel and the fractions were separated. The aqueous fraction was extracted with two 25 mL portions of 1-pentanol. The combined 1-pentanol fractions were dried over sodium sulfate and filtered to provide 1-(4-aminobutoxy)-2-butyl-1H-imidazo[4,5-c]quinolin-4-amine dissolved in 1-pentanol.

The maleate salt of 1-(4-aminobutoxy)-2-butyl-1H-imidazo[4,5-c]quinolin-4-amine was prepared by dissolving maleic acid (4.83 g) in 1-pentanol (50 mL) and adding it with stirring to the solution of 1-(4-aminobutoxy)-2-butyl-1H-imidazo[4,5-c]quinolin-4-amine in 1-pentanol. The resulting precipitate was collected by filtration and dried to yield 7.69 g of 1-(4-aminobutoxy)-2-butyl-1H-imidazo[4,5-c]quinolin-4-amine bis maleate salt. $^1$H-NMR (DMSO-d6): δ 0.96 (t, 3H), 1.44 (m, 2H), 1.7-1.95 (m, 4H), 2.02 (m, 2H), 2.8-3.1 (m, 4H), δ 4.43 (t, 2H), 6.07 (s, 4H), 7.57 (t, 1H), 7.73 (t, 1H), 7.80 (d, 1H), 8.16 (d, 1H). Broad peaks for the ammonium protons are seen at approximately δ7.8 and δ8.7.

Part E

The 1-(4-aminobutoxy)-2-butyl-1H-imidazo[4,5-c]quinolin-4-amine bis maleate salt (0.2 g) was suspended in 1-butanol (5 mL) and washed sequentially with 2×5 mL portions of a 5% sodium carbonate solution followed by 5 mL of a saturated sodium chloride solution. Succinimidyl 4-hydrazinonicotinate acetone hydrazone (SANH, 0.0216 g); available from Thermo Scientific, Rockford, Ill.; was added and the solution was stirred at ambient temperature for 17.5 hours. Analysis of the reaction by thin layer chromatography (silica gel, eluent of 1:1 methyl-tert-butylether : ethanol) showed only the presence of 1-(4-aminobutoxy)-2-butyl-1H-imidazo[4,5-c]quinolin-4-amine ($R_f$<0.05) and the desired product N-(4-{[4-amino-2-butyl-1H-imidazo[4,5-c]quinolin-1-yl]oxy}butyl)-6-(N'-isopropylidenehydrazino)nicotinamide ($R_f$ 0.30). The reaction was concentrated under reduced pressure and 5 mL of dichloromethane was added to the residue. Small amounts of insoluble material were removed by filtration and the sample was purified by column chromatography (silica gel, eluent of 1:1 methyl-tert-butylether:ethanol). The fractions containing product were combined and the solvent removed under reduced pressure to provide N-(4-{[4-amino-2-butyl-1H-imidazo[4,5-c]quinolin-1-yl]oxy}butyl)-6-(N'-isopropylidenehydrazino)nicotinamide as a light yellow solid (compound 1).

$^1$H NMR (chloroform-d) δ 8.59 (d, J=2.2 Hz, 1H), 7.81-8.15 (m, 3H), 7.75 (d, J=8.1 Hz, 1H), 7.48 (t, J=7.6 Hz, 1H), 7.28 (t, J=7.5 Hz, 1H), 7.20 (d, J=8.7 Hz, 1H), 6.57 (t, J=5.6 Hz, 1H), 5.61 (br. s., 2H), 4.24 (t, J=6.1 Hz, 2H), 3.55 (q, J=6.3 Hz, 2H), 2.88 (t, J=7.6 Hz, 2H), 1.93-2.12 (m, 5H), 1.74-1.93 (m, 7H), 1.37-1.54 (m, 2H), 0.96 (t, J=7.2 Hz, 3H).

Part F

The N-(4-{[4-amino-2-butyl-1H-imidazo [4,5-c]quinolin-1-yl]oxy}butyl)-6-(N'-isopropylidenehydrazino)nicotinamide from Part E was suspended in 1 mL of hydrochloric acid (0.6 M) and heated at 60° C. for 90 minutes. The resulting homogeneous solution was cooled to ambient temperature and the reaction was concentrated under reduced pressure. The resulting residue was dissolved in water and lyophilized to provide 43.6 mg of N-(4-{[4-amino-2-butyl-1H-imidazo[4,5-c]quinolin-1-yl]oxy}butyl)-6-hydazinonicotinamide hydrochloride salt as a yellow solid (Compound 2). MS (ESI) m/z 463.25661 (463.25645 calcd for $C_{24}H_{31}N_8O_2$, M+H$^+$).

Comparative Example A

Comparative Example A was prepared according to the methods of Examples 2 and 3, with the modification that succinimidyl 4-formylbenzoate (SFB) (Thermo Scientific, Rockford, Ill.) dissolved in dimethyl sulfoxide (DMSO) instead of Compound A was added to HA at a 10 fold molar excess during the Example 2 step.

The efficiency of incorporation of Compound 2 into HA through covalent conjugation was determined by using a UV spectrophotometric assay. The bis-aromatic hydrazone bond that is formed by covalent conjugation of HA-SFB with Compound 2 provides a distinctive chromophore. The chromophore has a maximal absorbance a 354 nm and a molar extinction coefficient equal to 29,000. The number of moles of compound 1 incorporated into the HA protein was calculated by dividing the measured absorbance of the conjugated HA-SFB-Compound 2 at 354 nm by the molar extinction coefficient of 29,000. The calculated moles of Compound 2 covalently conjugated to a mole of HA-SFB Protein was 6.1.

Comparison of Conjugation Methods of Example 3 and Comparative Example A

The effect of using Compound A in the covalently conjugated product, as compared to SFB, on final protein solubility and percent recovery is shown in Table I. The soluble protein measurement was determined as the amount of Comparative Example A or Example 3 recovered in the supernatant of a 100K x g centrifuged sample. The total protein measurement was determined as the amount of Comparative Example A or Example 3 in the sample prior to centrifugation. Soluble protein and total protein measurements were made using a Bicinchoninic Acid (BCA) Protein Assay (obtained from Thermo Scientific, Rockford, Ill.).

TABLE 1

| Protein Sample | Total Protein (µg/mL) | Soluble Protein (µg/mL) | Percent Recovery |
|---|---|---|---|
| Comparative Example A | 630.2 | 215.8 | 34.2% |
| Example 3 | 686.9 | 659.3 | 95.9% |

Example 4

Prophetic

The in vitro induction of interferon-α (IFN) and tumor necrosis factor (TNF) production in human peripheral mononuclear cells (PBMC) by the conjugated product of Example 3 can be determined using the following procedure. The PBMCs prepared from human volunteers can be placed in culture in 96 well microtiter plates. HA, the modified HA of Example 2, and the conjugate of Example 3 can be added to the wells at a final concentration of 1 µM protein. The cells can be incubated overnight at 37° C. The medium can be removed and IFN concentration (pg/mL) and TNF concentration (ng/mL) can be measured by ELISA assay.

Example 5

Prophetic

The vaccine adjuvant activity of the conjugate of Example 3 can be evaluated in Balb/C male mice (Charles River Laboratories, International, Wilmington, Mass.). Groups of 5 mice each can be immunized subcutaneously with 10 microgram of HA antigen in PBS (control), 10 microgram of Example 2 (control), or the conjugate of Example 3. The mice can be boosted with the same combinations 2 weeks and 4 weeks following the initial immunization. Three weeks and again at 12 weeks following the final boost, the mice can be bled and the HA-specific antibody titers determined. This determination can be performed by serial dilution of the serum samples by standard serum ELISA in HA-coated microtiter plates. The antibody data can be presented as the serum dilution achieving the end point (2X baseline) and is the geometric mean for the 5 mice per each group. As an index of TH1 bias of the immune response, HA-specific IgG1 and IgG2a subtypes can be measured, in addition to HA-specific total IgG.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A conjugate comprising a reaction product of:
a hydrazine- or hydrazide-substituted immune response modifier represented by formula:

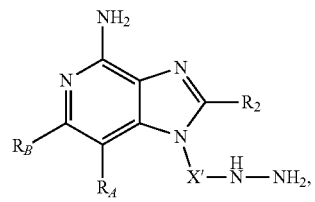

wherein when taken together $R_A$ and $R_B$ form a fused benzene ring that is unsubstituted, $R_2$ is hydrogen, alkyl, or alkoxyalkylenyl, and X' is —$X^1$—Y—$X^2$— or —$X^1$—Y—$X^2$—C(O)—, wherein $X^1$ is alkylene optionally interrupted by one or more —O— groups and optionally terminated by —O—; Y is —NH—C(O)—, and $X^2$ is alkylene, arylene, or heteroarylene;
a linker represented by formula:

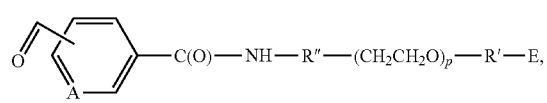

wherein A is CH or N, p is in a range from 1 to 50, R" is a bond or -alkylene-O—, R' is alkylene that is optionally interrupted or terminated with one or more amide or ether groups, and E is an amine- or thiol-reactive group; and
an antigen.

2. The conjugate of claim 1, wherein X' is —X¹—Y—X²—, wherein X¹ is alkylene optionally interrupted by one or more —O— groups and optionally terminated by —O—; Y is —NH—C(O)—, and X² is arylene or heteroarylene.

3. The conjugate of claim 1, wherein E is selected from the group consisting of maleimide, vinylsulfone, acrylamide, pyridyldisulfide, methyl sulfonyl disulfide, N-hydroxysuccinimide ester, sulfo-N-hydroxysuccinimide ester or a salt thereof, 4-nitrophenyl ester, acid chloride, acid bromide, acid anhydride, pentafluorophenyl ester, tetrafluorophenyl ester, N-hydroxybenzotriazole ester, iodoacetyl, bromoacetyl, chloroacetyl, succinimidyl carbonate, chloroformate, —OC(O)—O—CH(Cl)CCl₃, —OC(O)—O-(4-nitrophenyl), isocyanate, and thioisocyanate.

4. The conjugate of claim 3, wherein R' is alkylene having up to four carbon atoms, and E is an ester selected from the group consisting of N-hydroxysuccinimide ester, sulfo-N-hydroxysuccinimide ester or a salt thereof, 4-nitrophenyl ester, pentafluorophenyl ester, tetrafluorophenyl ester, and N-hydroxybenzotriazole ester.

5. The conjugate of claim 1, wherein the antigen is a protein.

6. The conjugate of claim 5, wherein a ratio of the linker to the protein is in a range from 30:1 to 1:3.

7. The conjugate of claim 1, wherein the conjugate is a vaccine.

8. A pharmaceutical composition comprising a pharmaceutically acceptable carrier and the conjugate of claim 1.

9. A conjugate comprising:
an immune response modifier represented by formula:

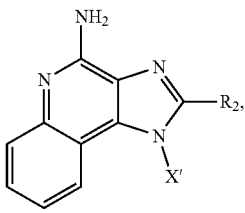

wherein $R_2$ is hydrogen, alkyl, or alkoxyalkylenyl, and X' is —X¹—Y—X²— or —X¹—Y—X²—C(O)—, wherein X¹ is alkylene optionally interrupted by one or more —O— groups and optionally terminated by —O—; Y is —NH—C(O)—, and X² is alkylene, arylene, or heteroarylene;
a linker represented by formula:

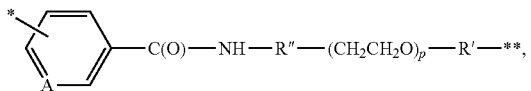

wherein A is CH or N, p is in a range from 1 to 50, R" is a bond or -alkylene-O—, and R' is a bond or alkylene that is optionally interrupted or terminated with one or more amide or ether groups; and
an antigen, wherein the X' is covalently attached to the linker at * through a hydrazone functional group, and wherein the antigen is covalently attached to the linker at ** through an amide, disulfide, urea, thiourea, carbamate, or a carbon-sulfur or carbon-nitrogen bond alpha to an amide or sulfone or directly attached to a succinimide ring.

10. The conjugate of claim 9, wherein the antigen is a protein.

11. The conjugate of claim 9, wherein p is in a range from 2 to 16.

12. The conjugate of claim 9, wherein the conjugate is a vaccine.

13. A pharmaceutical composition comprising a pharmaceutically acceptable carrier and the conjugate of claim 9.

14. A method of making the conjugate of claim 1, the method comprising:
combining an antigen with a linker to provide a modified antigen, wherein the linker is represented by formula:

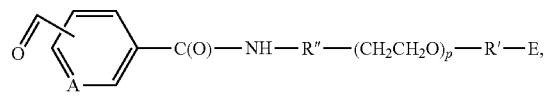

wherein A is CH or N, p is in a range from 1 to 50, R" is a bond or -alkylene-O—, R' is a bond or alkylene that is optionally interrupted or terminated with one or more amide or ether groups, and E is an amine- or thiol-reactive group; and
combining the modified antigen with a hydrazine- or hydrazide-substituted immune response modifier to provide the conjugate.

15. The method of claim 14, wherein E is selected from the group consisting of maleimide, vinylsulfone, acrylamide, pyridyldisulfide, methyl sulfonyl disulfide, N-hydroxysuccinimide ester, sulfo-N-hydroxysuccinimide ester or a salt thereof, 4-nitrophenyl ester, acid chloride, acid bromide, acid anhydride, pentafluorophenyl ester, tetrafluorophenyl ester, N-hydroxybenzotriazole ester, iodoacetyl, bromoacetyl, chloroacetyl, succinimidyl carbonate, chloroformate, —OC(O)—O—CH(Cl)CCl₃, —OC(O)—O-(4-nitrophenyl), isocyanate, and thioisocyanate.

16. The method of claim 15, wherein R' is alkylene having up to four carbon atoms, and E is an ester selected from the group consisting of N-hydroxysuccinimide ester, sulfo-N-hydroxysuccinimide ester or a salt thereof, 4-nitrophenyl ester, pentafluorophenyl ester, tetrafluorophenyl ester, and N-hydroxybenzotriazole ester.

17. A method of vaccinating an animal, the method comprising administering an effective amount of the pharmaceutical composition of claim 8 to the animal.

18. A method of inducing cytokine biosynthesis in an animal, the method comprising administering an effective amount of the pharmaceutical composition of claim 8 to the animal.

* * * * *

UNITED STATES PATENT AND TRADEMARK OFFICE
CERTIFICATE OF CORRECTION

PATENT NO. : 10,723,731 B2
APPLICATION NO. : 15/905367
DATED : July 28, 2020
INVENTOR(S) : Paul Wightman It is certified that error appears in the above-identified patent and that said Letters Patent is hereby corrected as shown below:

In the Specification

Column 9
Line 61, delete "-α, α-" and insert -- -α,α- --, therefor.

Column 12
Line 36, delete "—S(O)2;" and insert -- —S(O)2—; --, therefor.

Column 18
Line 41, delete "-[methylsulfonyl)" and insert -- -[(methylsulfonyl) --, therefor.
Line 44, delete "amino)}butyl," and insert -- amino}butyl, --, therefor.

Column 26
Line 59, delete "(e.," and insert -- (e.g., --, therefor.

Column 29
Lines 19-20, delete "-butoxycarbonylamino)" and insert
-- -butoxycarbonylamino). --, therefor.

Column 30
Line 17, delete "maintained" and insert -- maintained. --, therefor.

Column 31
Line 55, delete "animal" and insert -- animal. --, therefor.

Column 35
Line 46, delete "amine" and insert -- amine. --, therefor.

Column 36
Line 45, delete "amine" and insert -- amine. --, therefor.

Signed and Sealed this
Tenth Day of September, 2024

Katherine Kelly Vidal
*Director of the United States Patent and Trademark Office*

CERTIFICATE OF CORRECTION (continued)
U.S. Pat. No. 10,723,731 B2

Column 37
Line 30, delete "animal" and insert -- animal. --, therefor.
Line 54, delete "animal" and insert -- animal. --, therefor.
Line 64, delete "amine" and insert -- amine. --, therefor.

Column 39
Line 18, delete "Mo." and insert -- Mo.) --, therefor.

Column 41
Line 52, delete "Benzyl4-" and insert -- Benzyl 4- --, therefor.

Column 42
Line 29, delete "δ7.8 and δ8.7." and insert -- δ 7.8 and δ 8.7. --, therefor.
Line 54, delete "δ 8.59" and insert -- δ:8.59 --, therefor.
Line 61, delete "-imidazo [4,5-c]" and insert -- -imidazo[4,5-c] --, therefor.

In the Claims

Column 45
Line 2, in Claim 2, delete "X1is" and insert -- X1 is --, therefor.
Line 42, in Claim 9, delete "X1is" and insert -- X1 is --, therefor.